US011529328B2

(12) United States Patent
Ngo et al.

(10) Patent No.: US 11,529,328 B2
(45) Date of Patent: Dec. 20, 2022

(54) FORMULATIONS FOR PHARMACEUTICAL AGENTS

(71) Applicant: The Curators of the University of Missouri, Columbia, MO (US)

(72) Inventors: Albert N. Ngo, Long Beach, CA (US); Bi Botti Youan, Overland Park, KS (US)

(73) Assignee: The Curators of the University of Missouri, Columbia, MO (US)

( * ) Notice: Subject to any disclaimer, the term of this patent is extended or adjusted under 35 U.S.C. 154(b) by 107 days.

(21) Appl. No.: 16/847,960

(22) Filed: Apr. 14, 2020

(65) Prior Publication Data

US 2020/0323812 A1 Oct. 15, 2020

Related U.S. Application Data

(60) Provisional application No. 62/834,115, filed on Apr. 15, 2019.

(51) Int. Cl.
  *A61K 31/337* (2006.01)
  *A61K 9/19* (2006.01)
  *A61K 47/12* (2006.01)

(52) U.S. Cl.
  CPC .............. *A61K 31/337* (2013.01); *A61K 9/19* (2013.01); *A61K 47/12* (2013.01)

(58) Field of Classification Search
  None
  See application file for complete search history.

(56) References Cited

U.S. PATENT DOCUMENTS

| | | | |
|---|---|---|---|
| 2,895,990 | A | 7/1959 | Larrison |
| 8,912,228 | B2 | 12/2014 | Palepu |
| 10,213,447 | B2 | 2/2019 | Ngo et al. |
| 2009/0035356 | A1 | 2/2009 | Bui-Khac et al. |
| 2012/0027833 | A1 | 2/2012 | Zilberman |
| 2012/0258176 | A1 | 10/2012 | Sung et al. |
| 2013/0323179 | A1 | 12/2013 | Popov et al. |
| 2016/0361327 | A1* | 12/2016 | Ngo ..................... A61K 9/5036 |

FOREIGN PATENT DOCUMENTS

WO 2016201213 A1 12/2016

OTHER PUBLICATIONS

Ngo et al. Int J Pharm. vol. 545, pp. 329-341. (Year: 2018).*
Tang, X., Wang, G., Shi, R., Jiang, K., Meng, L., Ren, H., . . . & Hu, Y. (2016). Enhanced tolerance and antitumor efficacy by docetaxel-loaded albumin nanoparticles. Drug delivery, 23(8), 2686-2696.
Tapani, E., Taavitsainen, M., Lindros, K., Vehmas, T., & Lehtonen, E. (1996). Toxicity of ethanol in low concentrations: experimental evaluation in cell culture. Acta Radiologica, 37(6), 923-926.
Badal Tejedor, M., Nordgren, N., Schuleit, M., Pazesh, S., Alderborn, G., Millqvist-Fureby, A., & Rutland, M. W. (2017). Determination of interfacial amorphicity in functional powders. Langmuir, 33(4), 920-926.
Tsujino, I., Yamazaki, T., Masutani, M., Sawada, U., & Horie, T. (1999). Effect of Tween-80 on cell killing by etoposide in human lung adenocarcinoma cells. Cancer chemotherapy and pharmacology, 43(1), 29-34.
Tuomela, A., Hirvonen, J., & Peltonen, L. (2016). Stabilizing agents for drug nanocrystals: effect on bioavailability. Pharmaceutics, 8(2), 16.
Van Beilen, J. W. A., de Mattos, M. T., Hellingwerf, K. J., & Brul, S. (2014). Distinct effects of sorbic acid and acetic acid on the electrophysiology and metabolism of Bacillus subtilis. Applied and environmental microbiology, 80(19), 5918-5926.
Van Drooge, D. J., Hinrichs, W. L. J., Visser, M. R., & Frijlink, H. W. (2006). Characterization of the molecular distribution of drugs in glassy solid dispersions at the nano-meter scale, using differential scanning calorimetry and gravimetric water vapour sorption techniques. International journal of pharmaceutics, 310(1-2), 220-229.
Vo, C. L. N., Park, C., & Lee, B. J. (2013). Current trends and future perspectives of solid dispersions containing poorly water-soluble drugs. European journal of pharmaceutics and biopharmaceutics, 85(3), 799-813.
Wang, J., Yan, Z., Zhuo, K., & Lu, J. (1999). Partial molar volumes of some α-amino acids in aqueous sodium acetate solutions at 308.15 K. Biophysical chemistry, 80(3), 179-188.
Yhee, J. Y., Jeon, S., Yoon, H. Y., Shim, M. K., Ko, H., Min, J., . . . & Kwon, I. C. (2017). Effects of tumor microenvironments on targeted delivery of glycol chitosan nanoparticles. Journal of Controlled Release, 267, 223-231.
Zaske, L., Perrin, M. A., & Leveiller, F. (2001). Docetaxel: solid state characterization by X-ray powder diffraction and thermogravimetry. Le Journal de Physique IV, 11(PR10), Pr10-221.
Zhai, G., Wu, J., Xiang, G., Mao, W., Yu, B., Li, H., Piao, L., Lee, L.J., Lee, R.J., 2009. Preparation, characterization and pharmacokinetics of folate receptor-targeted liposomes for docetaxel delivery. J. Nanosci. Nanotechnol. 9, 2155-2161.
Zhang, P., Zhang, H., He, W., Zhao, D., Song, A., & Luan, Y. (2016). Disulfide-linked amphiphilic polymer-docetaxel conjugates assembled redox-sensitive micelles for efficient antitumor drug delivery. Biomacromolecules, 17(5), 1621-1632.
Zheng, J. Y., & Keeney, M. P. (2006). Taste masking analysis in pharmaceutical formulation development using an electronic tongue. International journal of pharmaceutics, 310(1-2), 118-124.
Y.L. Lee, T. Cesario, J. Owens, E. Shanbrom, and L.D. Thrupp. Antibacterial activity of citrate and acetate. Nutrition. 18:665-666 (2002).
G. Freeh, L.V. Allen, Jr., M.L. Stiles, and R.S. Levinson. Sodium acetate as a preservative in protein hydrolysate solutions. American journal of hospital pharmacy. 36:1672-1675 (1979).
H. Karaca, M.B. Perez-Gago, V. Taberner, and L. Palou. Evaluating food additives as antifungal agents against Monilinia fructicola in vitro and in hydroxypropyl methylcellulose-lipid composite edible coatings for plums. International journal of food microbiology. 179:72-79 (2014).

(Continued)

*Primary Examiner* — Katherine Peebles
(74) *Attorney, Agent, or Firm* — C. John Brannon; Brannon Sowers & Cracraft PC

(57) ABSTRACT

A method for forming crystalline solid dispersions (CSDs) of a pharmaceutical agent with low water solubility is described. The properties of the CSDs are described. Also described is the enhancement of bioavailability of the pharmaceutical agent resulting from formation of the CSD.

14 Claims, 11 Drawing Sheets

(56) References Cited

OTHER PUBLICATIONS

C. Costa, A. Conte, and M.A. Del Nobile. Effective preservation techniques to prolong the shelf life of ready-to-eat bysters. J Sci Food Agric. 94:2661-2667 (2014).
D. Fong, M.B. Ariganello, J. Girard-Lauziere, and C.D. Hoemann. Biodegradable chitosan microparticles induce delayed STAT-1 activation and lead to distinct cytokine responses in differentially polarized human macrophages in vitro. Acta biomaterialia(2014).
A. Smith, M. Perelman, and M. Hinchcliffe. Chitosan: a promising safe and immune-enhancing adjuvant for intranasal vaccines. Human vaccines & immunotherapeutics. 10:797-807 (2014).
H. Zheng, C. Tang, and C. Yin. Exploring advantages/disadvantages and improvements in overcoming gene delivery barriers of amino Acid modified trimethylated chitosan. Pharm Res. 32:2038-2050 (2015).
J. Meng, T.F. Sturgis, and B.B. Youan. Engineering tenofovir loaded chitosan nanoparticles to maximize microbicide mucoadhesion. Eur J Pharm Sci. 44:57-67 (2011).
A.N. Ngo, M.J. Ezoulin, I. Youm, and B.B. Youan. Optimal Concentration of 2,2,2-Trichloroacetic Acid for Protein Precipitation Based on Response Surface Methodology. Journal of analytical & bioanalytical techniques 5:(2014).
A.A. Date and, et al., Biomaterials. 34:6202-6228 (2013).
R.S. Ankita kapoor, Pankaj Sharma, Paaras Gupta. BCS Classification System: Benchmark for Solubility and Permeability. Indo American Journal of Pharmaceutical Research 4:(2014).
X. Wang, C. Zheng, Z. Wu, D. Teng, X. Zhang, Z. Wang, and C. Li. Chitosan-NAC nanoparticles as a vehicle for nasal absorption enhancement of insulin. Journal of biomedical materials research Part B, Applied biomaterials. 88:150-161 (2009).
A. Rampino, M. Borgogna, P. Blasi, B. Bellich, and A. Cesaro. Chitosan nanoparticles: preparation, size evolution and stability. Int J Pharm. 455:219-228 (2013).
M. Dionisio, C. Cordeiro, C. Remunan-Lopez, B. Seijo, A.M. Rosa da Costa, and A. Grenha. Pullulan-based nanoparticles as carriers for transmucosal protein delivery. Eur J Pharm Sci. 50:102-113 (2013).
B. D. Cullity S.R. Stock. Elements X-ray Diffraction. Book, ISBN 0-12-352651-5:309 (2001).
J.S. Fritz. Titration of Bases in Nonaqueous Solvents. Analytical Chemistry. 22:(1950).
G.A.Harlow and D.B. Bruss. Titration of Weak Acids in Nonaqueous Solvents: Potentiometric Studies in Inert Solvents. Analytical Chemistry 30:(1958).
P. Costa and J.M. Sousa Lobo. Modeling and comparison of dissolution profiles. Eur J Pharm Sci. 13:123-133 (2001).
A.S. Wadajkar, T. Kadapure, Y. Zhang, W. Cui, K.T. Nguyen, and J. Yang. Dual-imaging enabled cancer-targeting nanoparticles. Adv Healthc Mater. 1:450-456 (2012).
S.K. Panda, S. Kumar, N.C. Tupperwar, T. Vaidya, A. George, S. Rath, V. Bal, and B. Ravindran. Chitohexaose activates macrophages by alternate pathway through TLR4 and blocks endotoxemia. PLoS Pathog. 8:e1002717 (2012).
S. Lanone, F. Rogerieux, J. Geys, A. Dupont, E. Maillot-Marechal, J. Boczkowski, G. Lacroix, and P. Hoet. Comparative toxicity of 24 manufactured nanoparticles in human alveolar epithelial and macrophage cell lines. Part Fibre Toxicol. 6:14 (2009).
E. Borenfreund and J.A. Puemer. Toxicity determined in vitro by morphological alterations and neutral red absorption. Toxicol Lett. 24:119-124 (1985).
E. Vega-Avila and M.K. Pugsley. An overview of colorimetric assay methods used to assess survival or proliferation of mammalian cells. Proc West Pharmacol Soc. 54:10-14 (2011).
L. Connelly, M. Palacios-Callender, C. Ameixa, S. Moncada, and A.J. Hobbs. Biphasic regulation of NF-kappa B activity underlies the pro- and anti-inflammatory actions of nitric oxide. J Immunol. 166:3873-3881 (2001).
I.D. Kim and B.J. Ha. Paeoniflorin protects RAW 264.7 macrophages from LPS-induced cytotoxicity and genotoxicity. Toxicol In Vitro. 23:1014-1019 (2009).
A. Introini, C. Vanpouille, A. Lisco, J.C. Grivel, and L. Margolis. Interleukin-7 facilitates HIV-1 transmission to cervico-vaginal tissue ex vivo. PLoS pathogens. 9:e1003148 (2013).
N. Poth, V. Seiffart, G. Gross, H. Menzel, and W. Dempwolf. Biodegradable Chitosan Nanoparticle Coatings on Titanium for the Delivery of BMP-2. Biomolecules. 5:3-19 (2015).
E.N. Koukaras, S.A. Papadimitriou, D.N. Bikiaris, and G.E. Froudakis. Insight on the formation of chitosan nanoparticles through ionotropic gelation with tripolyphosphate. Molecular pharmaceutics. 9:2856-2862 (2012).
M.H. Ki, J.E. Kim, Y.N. Lee, S.M. Noh, S.W. An, H.J. Cho, and D.D. Kim. Chitosan-based hybrid nanocomplex for siRNA delivery and its application for cancer therapy. Pharm Res. 31:3323-3334 (2014).
C. Giovino, I. Ayensu, J. Tetteh, and U.S. Boateng. An integrated buccal delivery system combining chitosan films impregnated with peptide loaded PEG-b-PLA nanoparticles. Colloids and surfaces B, Biointerfaces. 112:9-15 (2013).
Y. Zu, Q. Zhao, X. Zhao, S. Zu, and L. Meng. Process optimization for the preparation of oligomycin-loaded folate-conjugated chitosan nanoparticles as a tumor-targeted drug delivery system using a two-level factorial design method. International journal of nanomedicine. 6:3429-3441 (2011).
J. Cho, M.C. Heuzey, A. Begin, and P.J. Carreau. Physical gelation of chitosan in the presence of beta-glycerophosphate: the effect of temperature. Biomacromolecules. 6:3267-3275 (2005).
P.D. Constable. Acid-base assessment: when and how to apply the Henderson-Hasselbalch equation and strong ion difference theory. The Veterinary clinics of North America Food animal practice. 30:295-316, v (2014).
S. Magder and A. Emami. Practical approach to physical-chemical Acid-base management. Stewart at the bedside. Annals of the American Thoracic Society. 12:111-117 (2015).
Fwu-Long Mi, Tsung-Bi Wong, Shiang-Fang Jang, Sung-Tao Lee, Kai-Tai Lu. Chitosan-Polyelectrolyte Complexation for the Preparation of Gel Beads and Controlled Release of Anticancer Drug. II. Effect of pH-Dependent Ionic Crosslinking or Interpolymer Complex Using Tripolyphosphate or Polyphosphate as Reagent. Journal of Applied Polymer Sciences. 74:1093-1107 (1999).
Amat, S., Bougnoux, P., Penault-Llorca, F., Fetissof, F., Cure, H., Kwiatkowski, F., . . & Chollet, P. (2003). Neoadjuvant docetaxel for operable breast cancer induces a high pathological response and breast-conservation rate. British journal of cancer, 88(9), 1339-1345.
Borner, M. M., Schneider, E., Pimia, F., Sartor, O., Trepel, J. B., & Myers, C. E. (1994). The detergent Triton X-100 induces a death pattern in human carcinoma cell lines that resembles cytotoxic lymphocyte-induced apoptosis. FEBS letters, 353(2), 129-132.
Chen, H., Khemtong, C , Yang, X., Chang, X., & Gao, J. (2011). Nanonization strategies for poorly water-soluble drugs. Drug discovery today, 16(7-8), 354-360.
Cheow, W. S., Kiew, T. Y., Yang, Y., & Hadinoto, K. (2014). Amorphization strategy affects the stability and supersaturation profile of amorphous drug nanoparticles. Molecular pharmaceutics, 11(5), 1611-1620.
Chiou, W. L., & Riegelman, S. (1971). Pharmaceutical applications of solid dispersion systems Journal of pharmaceutical sciences, 60(9), 1281-1302.
Craig, D. Q. (2002). The mechanisms of drug release from solid dispersions in water-soluble polymers. International journal of pharmaceutics, 231(2), 131 144.
Curtin, V., Amharar, Y., Hu, Y., Erxleben, A., McArdle, P., Caron, V., . . . & Healy, A. M. (2013). Investigation of the capacity of low glass transition temperature excipients to minimize amorphization of sulfadimidine on comilling. Molecular pharmaceutics, 10(1), 386-396.
Desktop, X. (1997). ray Diffractometer "MiniFlex+" The Rigaku Journal, 14(1), 29-36.

(56) References Cited

OTHER PUBLICATIONS

Dhapte, V., & Mehta, P. (2015). Advances in hydrotropic solutions: an updated review. St. Petersburg Polytechnical University Journal: Physics and Mathematics, 1(4), 424-435.

Dutta, A. K., & Belfort, G. (2007). Adsorbed gels versus brushes: viscoelastic differences. Langmuir, 23(6), 3088-3094.

Garg, N. K., Tyagi, R. K., Sharma, G., Jain, A., Singh, B., Jain, S., & Katare, O. P. (2017). Functionalized lipid-polymer hybrid nanoparticles mediated codelivery of methotrexate and aceclofenac: a synergistic effect in breast cancer with improved pharmacokinetics attributes. Molecular pharmaceutics, 14(6), 1883-1897.

Garg, N. K., Singh, B., Kushwah, V., Tyagi, R. K., Sharma, R., Jain, S., & Katare, O. P. (2016). The ligand (s) anchored lipobrid nanoconstruct mediated delivery of methotrexate: an effective approach in breast cancer therapeutics. Nanomedicine: Nanotechnology, Biology and Medicine, 12(7), 2043-2060.

Gonçalves, C., Gomez, J. P., Même, W., Rasolonjatovo, B., Gosset, D., Nedellec, S., . . . & Midoux, P. (2017). Curcumin/poly (2-methyl-2-oxazoline-b-tetrahydrofuran-b-2-methyl-2-oxazoline) formulation: An improved penetration and biological effect of curcumin in F508del-CFTR cell lines. European Journal of Pharmaceutics and Biopharmaceutics, 117, 168-181.

Hansen, C. M. (1967). The three dimensional solubility parameter. Danish Technical: Copenhagen, 14.

Huynh, L., Grant, J., Leroux, J. C., Delmas, P., & Allen, C. (2008). Predicting the solubility of the anti-cancer agent docetaxel in small molecule excipients using computational methods Pharmaceutical research, 25(1), 147-157.

Jensen, K. T., Larsen, F. H., Cornett, C., Lobmann, K., Grohganz, H., & Rades, T. (2015). Formation mechanism of coamorphous drug-amino acid mixtures. Molecular pharmaceutics, 12(7), 2484-2492.

Johnston, C. S., & Gaas, C. A. (2006). Vinegar: medicinal uses and antiglycemic effect. Medscape General Medicine, 8(2), 61.

Kalepu, S., & Nekkanti, V. (2015). Insoluble drug delivery strategies: review of recent advances and business prospects. Acta Pharmaceutica Sinica B, 5(5), 442-453.

Karczmarczyk, A., Haupt, K., & Feller, K. H. (2017). Development of a QCM-D biosensor for Ochratoxin A detection in red wine Talanta, 166, 193-197.

Kauppinen, A., Broekhuis, J., Grasmeijer, N., Tonnis, W., Ketolainen, J., Frijlink, H. W., & Hinrichs, W. L. (2018). Efficient production of solid dispersions by spray drying solutions of high solid content using a 3-fluid nozzle. European Journal of Pharmaceutics and Biopharmaceutics, 123, 50-58.

Kawabata, Y., Yamamoto, K., Debari, K., Onoue, S., & Yamada, S. (2010). Novel crystalline solid dispersion of tranilast with high photostability and improved oral bioavailability. European journal of pharmaceutical sciences, 39(4), 256-262.

Knowles, S. E., Jarrett, L G., Filsell, O. H., & Ballard, F. J. (1974). Production and utilization of acetate in mammals. Biochemical Journal, 142(2), 401-411.

Koya, Y., Uchida, S., Machi, Y., Shobu, Y., Namiki, N., & Kotegawa, T. (2016). Prediction of drug interaction between oral adsorbent AST-120 and concomitant drugs based on the in vitro dissolution and in vivo absorption behavior of the drugs. European journal of clinical pharmacology, 72(11), 1353-1361.

Kucukzeybek, Y., Gul, M. K., Cengiz, E., Erten, C., Karaca, B., Gorumlu, G., . . . & Uslu, R. (2008). Enhancement of docetaxel-induced cytotoxicity and apoptosis by all-trans retinoic acid (ATRA) through downregulation of survivin (BIRC5), MCL-1 and LTbeta-R in hormone-and drug resistant prostate cancer cell line, DU-145. Journal of experimental & clinical cancer research, 27(1), 1-8.

Kulkarni, Y. M., Yakisich, J. S., Azad, N., Venkatadri, R., Kaushik, V., O'Doherty, G., & Iyer, A. K. V. (2017). Anti-tumorigenic effects of a novel digitoxin derivative on both estrogen receptor-positive and triple-negative breast cancer cells. Tumor Biology, 39(6), 1010428317705331.

Kumar, V. S., Raja, C., & Jayakumar, C. (2014). A reviewon solubility enhancement using hydrotropic phenomena. Int. J. Pharm. Pharm. Sci, 6(6), 1-7.

LaFountaine, J. S., Prasad, L. K., Miller, D. A., McGinity, J. W., & Williams III, R. O. (2017). Mucoadhesive amorphous solid dispersions for sustained release of poorly water soluble drugs. European Journal of Pharmaceutics and Biopharmaceutics, 113, 157-167.

Löbmann, K., Laitinen, R., Grohganz, H., Gordon, K. C., Strachan, C., & Rades, T. (2011). Coamorphous drug systems: enhanced physical stability and dissolution rate of indomethacin and naproxen. Molecular pharmaceutics, 8 (5), 1919-1928.

Lyseng-Williamson, K. A., & Fenton, C. (2005). Docetaxel. Drugs, 65(17), 2513-2531.

Malleswara Reddy, A., Banda, N., Govind Dagdu, S., Rao, D. V., Kocherlakota, C. S., & Krishnamurthy, V. (2010). Evaluation of the pharmaceutical quality of docetaxel injection using new stability indicating chromatographic methods for assay and impurities. Scientia pharmaceutica, 78(2), 215-232.

Marano, S., Barker, S. A., Raimi-Abraham, B. T., Missaghi, S., Rajabi-Siahboomi, A., & Craig, D. Q. (2016). Development of micro-fibrous solid dispersions of poorly water-soluble drugs in sucrose using temperature-controlled centrifugal spinning. European Journal of Pharmaceutics and Biopharmaceutics, 103, 84-94.

Martinez, L. M., Videa, M., Silva, T. L., Castro, S., Caballero, A., Lara-Diaz, V. J., & Castorena-Torres, F. (2017). Two-phase amorphous-amorphous solid drug dispersion with enhanced stability, solubility and bioavailability resulting from ultrasonic dispersion of an immiscible system. European Journal of Pharmaceutics and Biopharmaceutics, 119, 243-252.

Meng, J., Agrahari, V., Ezoulin, M. J., Purohit, S. S., Zhang, T., Molteni, A., . . . & Youan, B. B. C. (2017). Spray-dried thiolated chitosan-coated sodium alginate multilayer microparticles for vaginal HIV microbicide delivery. The AAPS journal, 19(3), 692-702.

Merkle, F., Böttcher, W., & Hetzer, R. (2003). Prebypass filtration of cardiopulmonary bypass circuits: an outdated technique?. Perfusion, 18(1_suppl), 81-88.

Minofar, B., Jungwirth, P., Das, M. R., Kunz, W., & Mahiuddin, S. (2007). Propensity of formate, acetate, benzoate, and phenolate for the aqueous solution/vapor interface: Surface tension measurements and molecular dynamics simulations. The Journal of Physical Chemistry C, 111(23), 8242-8247.

Mirza, A., & Mithal, N. (2011). Alcohol intoxication with the new formulation of docetaxel. Clinical oncology (Royal College of Radiologists (Great Britain)), 23(8), 560-561.

Naguib, Y. W., Rodriguez, B. L., Li, X., Hursting, S. D., Williams III, R. O., & Cui, Z. (2014). Solid lipid nanoparticle formulations of docetaxel prepared with high melting point triglycerides: in vitro and in vivo evaluation. Molecular pharmaceutics, 11(4), 1239-1249.

National Academies of Sciences, Engineering, and Medicine. (2015). Application of modern toxicology approaches for predicting acute toxicity for chemical defense.

Neavyn, M. J., Boyer, E. W., Bird, S. B., & Babu, K. M. (2013). Sodium acetate as a replacement for sodium bicarbonate in medical toxicology: a review. Journal of Medical Toxicology, 9(3), 250-254.

Ngo, A. N., Ezoulin, M. J., Murowchick, J. B., Gounev, A. D., & Youan, B. B. C. (2016). Sodium acetate coated tenofovir-loaded chitosan nanoparticles for improved physico-chemical properties. Pharmaceutical research, 33(2), 367-383.

Nikkhah, M., Strobl, J. S., Schmelz, E. M., Roberts, P. C., Zhou, H., & Agah, M. (2011). MCF10Aand MDA-MB-231 human breast basal epithelial cell co-culture in silicon micro-arrays. Biomaterials, 32(30), 7625-7632.

Rabinow, B. E. (2004). Nanosuspensions in drug delivery. Nature reviews Drug discovery, 3(9), 785-796.

Saal, W., Ross, A., Wyttenbach, N., Alsenz, J., & Kuentz, M. (2017). A systematic study of molecular interactions of anionic drugs with a dimethylaminoethyl methacrylate copolymer regarding solubility enhancement. Molecular pharmaceutics, 14(4), 1243-1250.

Selvamuthukumar, S., Anandam, S., Krishnamoorthy, K., & Rajappan, M. (2012). Nanosponges: A novel class of drug delivery system-review. Journal of Pharmacy & Pharmaceutical Sciences, 15(1), 103-111.

(56) References Cited

OTHER PUBLICATIONS

Shah, S. M., Jain, A. S., Kaushik, R., Nagarsenker, M. S., & Nerurkar, M. J. (2014). Preclinical formulations: insight, strategies, and practical considerations. Aaps Pharmscitech, 15(5), 1307-1323.

Sharafi, M., Hayes, J. E., & Duffy, V. B. (2013). Masking vegetable bitterness to improve palatability depends on vegetable type and taste phenotype. Chemosensory perception, 6(1), 8-19.

Sumer Bolu, B., Manavoglu Gecici, E., & Sanyal, R. (2016). Combretastatin A-4 conjugated antiangiogenic micellar drug delivery systems using dendron-polymer conjugates. Molecular pharmaceutics, 13(5), 1482-1490.

Sunder, S., & Nair, R. (2016). Methods of nanonization of drugs for enhancing their dissolution. Eur. J. Adv. Eng. Tech, 3(8), 101-110.

Tan, Q., Liu, X., Fu, X., Li, Q., Dou, J., & Zhai, G. (2012). Current development in nanoformulations of docetaxel. Expert opinion on drug delivery, 9(8), 975-990.

W. Hu, L. Ding, J. Cao, L. Liu, Y. Wei, and Y. Fang. Protein binding-induced surfactant aggregation variation: a new strategy of developing fluorescent aqueous sensor for proteins. ACS applied materials & interfaces. 7:4728-4736 (2015).

T. C. Padhiyar and S. B. Thakore. Recovery of Acetic Acid From Effluent via Freeze Crystallization. Internationnal Journal of Scientific Engineering and Technology 2:211-215 (2013).

Paula Atkin's Physical Chemistry, ninth edition. Book, ISBN 978-0-19-954337-3:196 (2010).

Dana W. Mayo, F.A.Miller, Robert W. Hannah. Course notes on the interpretaion of Infrared and Raman Spectra. Wiley&Sons Publication:210-213 (2004).

T. S. Cameron. The crystal structure of sodium acetate trihydrate. Acta Crystallographica Section B. 32:87-90 (1976).

B. D. Cullity and S.R. Stock. Elements X-Ray Diffraction Book, ISBN 0-201-61091-1. 3 296 (2001).

M D. Chavanpatil, P. Jain, S. Chaudhari, R. Shear, and P.R. Vavia. Novel sustained release, swellable and bioadhesive gastroretentive drug delivery system for ofloxacin. Int J Pharm. 316:86-92 (2006).

S. Joshi and H.U. Petereit. Film coatings for taste masking and moisture protection. Int J Pharm. 457:395-406 (2013).

S.T. Gunawan, K. Liang, G.K. Such, A.P. Johnston, M.K. Leung, J. Cui, and F. Caruso. Engineering enzyme-cleavable hybrid click capsules with a pH-sheddable coating for intracellular degradation. Small. 10:4080-4086 (2014).

A.M. Elbarbary and T.B. Mostafa. Effect of gamma-rays on carboxymethyl chitosan for use as antioxidant and preservative coating for peach fruit. Carbohydrate polymers. 104:109-117 (2014).

Shalmashi et al., "Solubility of Caffeine in Water, Ethyl Acetate, Ethanol, Carbon Tetrachloride, Methanol, Chloroform, Dichloromethane, and Acetone Between 298 and 323 K", 2010, Latin American Applied Research, vol. 40, No. 3, pp. 283-285.

U. Stange, C. Fuhrling, and H. Gieseler, T -57 (2014). taste masking of naproxen sodium granules by fluid-bed coating. Pharmaceutical development and technology. 19:137-147 (2014).

Ruiz-Caro, Robert, Veiga-Ochoa, Maria Dolores. Characterization and Dissolution Study of Chitosan Freeze-Dried Systems for Drug Controlled Release. Molecules. 14:4370-4386 (2009).

Zinc Acetate. In Hawley's Condensed Chemical Dictionary, R. J. Lewis (ed.), 2007.

Divya et al., "Design, Formulation and Characterization of Tenofovir Microemulsion as Oral Drug Delivery", 2014, International Journal of Pharmacy Review and Research, vol. 4, issue 1, pp. 1-5.

Veyries et al., "Controlled release of vancomycin from Poloxamer 407 gels", 1999, International Journal of Pharmaceutics, vol. 192, pp. 183-193.

Engels, F. K., Mathot, R. A., & Verweij, J. (2007). Alternative drug formulations of docetaxel: a review. Anti-cancer drugs, 18(2), 95-103.

* cited by examiner

FORMULATIONS FOR PHARMACEUTICAL AGENTS

CROSS-REFERENCES TO RELATED APPLICATIONS

This application claims the benefit under 35 U.S.C. § 119(e) of U.S. Provisional Application No. 62/834,115, filed Apr. 15, 2019, the entirety of the disclosure of which is incorporated herein by reference.

TECHNICAL FIELD

This application relates to methods for formulating compounds with low water solubility to yield compositions that improved solubility or dispersion of those compounds in aqueous mixtures.

BACKGROUND

In the drug development pipeline, nearly 90% of new active chemical entities are considered poorly water soluble drugs based on the biopharmaceutics classification system (BCS) (Kalepu and Nekkanti, 2015; Tuomela et al., 2016). Hydrophobic drugs exhibit mostly crystalline structure. Those crystalline structures form tightly bonded atoms with high cohesive energy. In addition, hydrophobic drugs exhibit low aqueous solubility, poor absorption, limited dissolution and undesirable drug crystal size growth (Badal Tejedor et al., 2017; Cheow et al., 2014; Curtin et al., 2013; Jensen et al., 2015; Lobmann et al., 2011), resulting in low bioavailability and efficacy. These drugs are not suitable for intravenous (IV) administration because those poorly water-soluble solid aggregated drugs can potentially lead to thrombosis or stroke.

The term solid dispersion in pharmaceutical formulation is defined as systems where the drug is finely dispersed in a carrier or excipient (Baird and Taylor, 2012; Kauppinen et al., 2017; Marano et al., 2016; Martinez et al., 2017). When the poorly water soluble drug is dispersed in a crystalline-carrier, amorphous-polymer-carrier, surfactant polymer carrier, and poorly water soluble-polymer carrier, the solid dispersion technique is called first, second, third and fourth generation solid dispersions, respectively (Vo et al., 2013).

In an amorphous solid dispersion (ASD), the hydrophobic drug is dispersed in an amorphous carrier (Baird and Taylor, 2012; LaFountaine et al., 2017). Classically, the ASD technique involves the dispersion of a crystalline or an amorphous drug in an amorphous polymeric matrix (Baird and Taylor, 2012; Goncalves et al., 2017; Jensen et al., 2015; Saal et al., 2017).

In contrast to ASD, a crystalline solid dispersion (CSD) are systems where the carrier is crystalline not amorphous (Baird and Taylor, 2012; Vo et al., 2013). When, the dispersed drug is either amorphous or crystalline particles or separate molecules in the crystalline carrier, the CSD system is an amorphous precipitation in a crystalline carrier (APCC), an eutectic, and a crystalline solid solution (CSS), respectively (Chiou and Riegelman, 1971; Vo et al., 2013).

Sekiguchi and Obi, reported the first eutectic CSD where urea used as the crystalline carrier was blended with a crystalline sulphathiazole following heating and fusion of the mixture above the eutectic point and rapid cooling of the eutectic mixture (Chiou and Riegelman, 1971; Vo et al., 2013). This latter process, known as the melting method has the advantage of not using a solvent, however the fusion melting method exhibits several limitations.

One limitation is the thermostability and physical degradation of the active pharmaceutical ingredient during the melting, crushing and milling of the resulting solid eutectic mass, respectively (Vo et al., 2013). In addition, the dispersed drug may have a propensity to rapidly crystallize when the carrier-drug mixture is not at the exact eutectic molar composition (Craig, 2002; Vo et al., 2013).

A CSD system is a promising strategy to improve drugs bioavailability when they are, either, molecularly, amorphously or crystalline particulate matter dispersed in a highly water soluble carrier (Kawabata et al., 2010). There are three main methods for solid dispersion especially, the melting method, the solvent method and the melting/solvent method (Vo et al., 2013). A solvent method involving freeze-drying or other drying method may circumvent some of the limitations of the melting method because it may cause less thermal degradation of the drug (van Drooge et al., 2006; Vo et al., 2013).

light) respectively (n=3). *P<0.05 vs media,  P<0.01 vs media, * P<0.001 vs media.

(b) Percent MCF 10A cell viability (% control) treated 48 h with the different formulations: (from left to right) Blank SA/PEG300 (pattern fill, weave), Blank Tween 80/EtOH (pattern fill, large grid), crystal solid dispersion of docetaxel (C-DXT) (pattern fill, solid diamond grid), and Simulated clinical DXT (pattern fill, Horizontal stripes: light) respectively (n=3). *P<0.05 vs media, P<0.01 vs media, *P<0.001 vs media.

Figure 10:
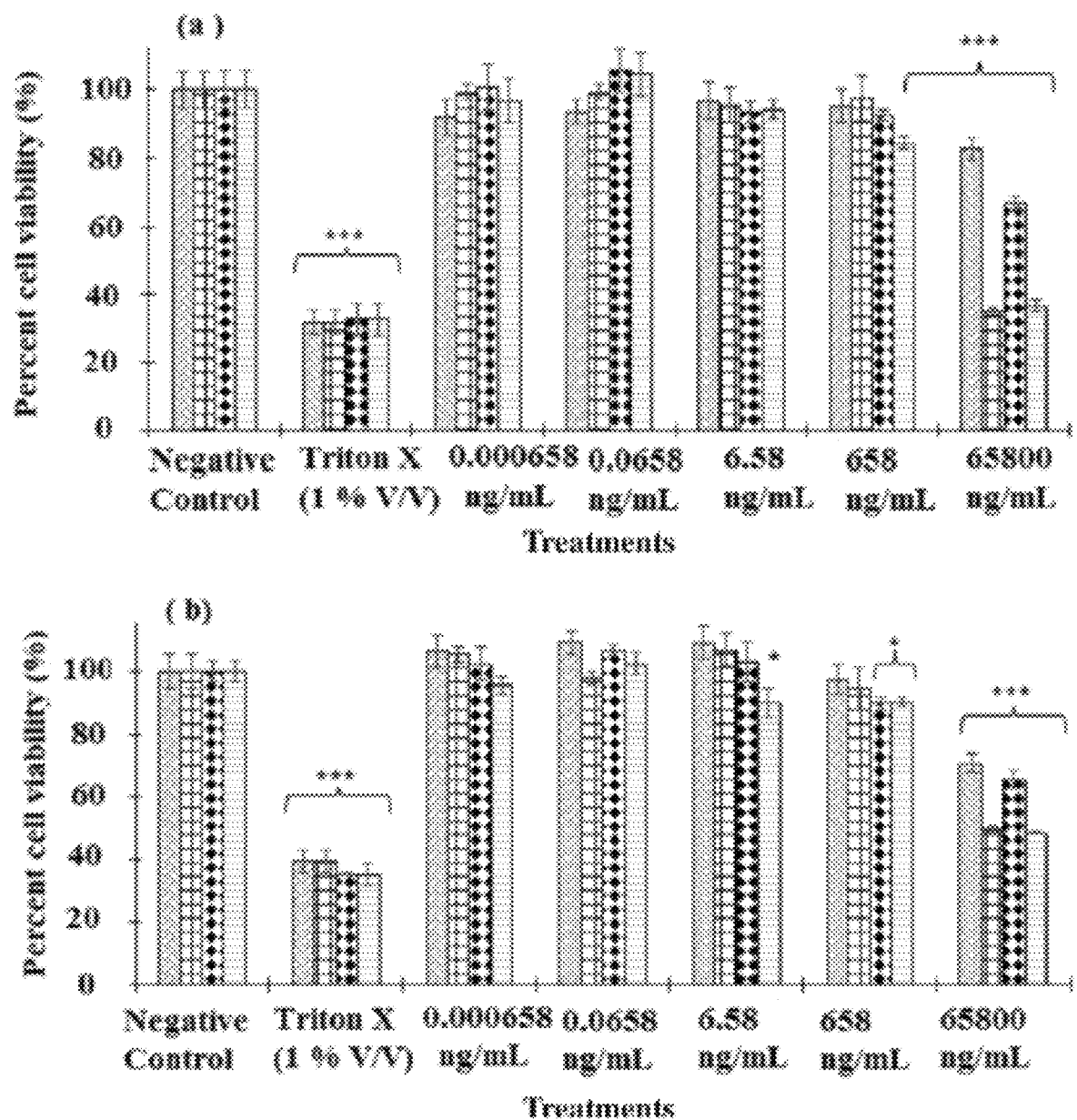

FIG. 10. (a) Percent MCF 7 cell viability (% control) treated 24 h with the different formulations: (from left to right) Blank SA/PEG300 (pattern fill, weave), Blank Tween 80/EtOH (pattern fill, large grid), crystal solid dispersion of docetaxel (C-DXT) (pattern fill, solid diamond grid), and Simulated clinical DXT (pattern fill, Horizontal stripes: light) respectively (n=3). *P<0.05 vs media, P<0.01 vs media, *P<0.001 vs media.

(b) Percent MCF 10A cell viability (% control) treated 48 h with the different formulations: (from left to right) Blank SA/PEG300 (pattern fill, weave), Blank Tween 80/EtOH (pattern fill, large grid), crystal solid dispersion of docetaxel (CDXT) (pattern fill, solid diamond grid), and Simulated clinical DXT (pattern fill, Horizontal stripes: light) respectively (n=3). *P<0.05 vs media, P<0.01 vs media, *P<0.001 vs media.

Figure 11:
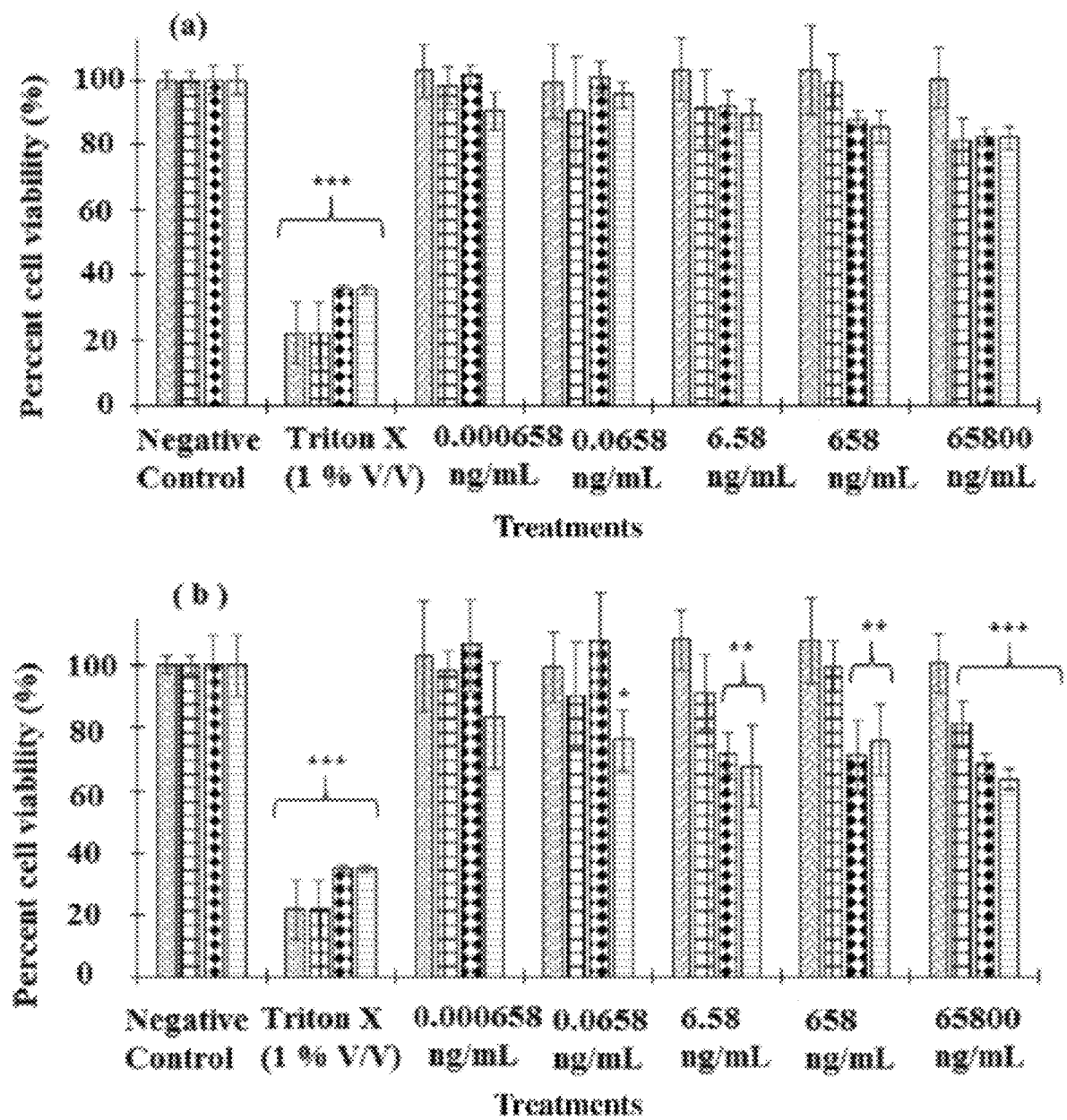

FIG. 11. (a) Percent MDA-MB 468 cell viability (% control) treated 24 h with the different formulations: from left to right Blank SA/PEG (pattern fill, weave), Blank Tween 80/EtOH (pattern fill, large grid), crystal solid dispersion of docetaxel (C-DXT) (pattern fill, solid diamond grid), and Simulated clinical DXT (pattern fill, Horizontal stripes: light) respectively (n=3). *P<0.05 vs media, P<0.01 vs media, *P<0.001 vs media.

(b) Percent MCF 10A cell viability (% control) treated 48 h with the different formulations: from left to right Blank SA/300PEG (pattern fill, weave), Blank Tween 80/EtOH (pattern fill, large grid), crystal solid dispersion of docetaxel (CDXT) (pattern fill, solid diamond grid), and Simulated clinical DXT (pattern fill, Horizontal stripes: light) respectively (n=3). *P<0.05 vs media, P<0.01 vs media, *P<0.001 vs media.

DETAILED DESCRIPTION

Several non-limiting, illustrative embodiments of the invention are described by the following clauses:

1. A process for improving the aqueous availability of a compound with low water solubility by forming a crystalline solid dispersion (CSD) of the compound, the process comprising the steps:

(a) forming a solution of the compound and one or more acetate salts selected from the group consisting of LiOAc, NaOAc, KOAc, and CsOAc in glacial acetic acid optionally containing a solvent selected from the list of acetonitrile, methyl acetate, ethyl acetate, n-propyl acetate, n-butyl acetate, tetrahydrofuran, methanol, ethanol, n-propanol, isopropanol, n-butanol, sec-butanol, dimethyl formamide, acetone, and 2-butanone; and (b) removing the acetic acid and optional solvent from the solution from step (a) by freeze-drying or spray-drying to yield a crystalline solid dispersion (CSD) of the compound.

2. The process of clause 1 wherein the improved availability is improved aqueous dispersion of the compound.

3. The process of clause 1 wherein the improved aqueous availability is improved aqueous solubility of the compound.

4. The process of any one of clauses 1 to 3 wherein the compound is a bioactive compound.

5. The process of any one of the preceding clauses the bioactive compound is a pharmaceutical compound.

6. The process of any one of the preceding clauses wherein the pharmaceutical compound is selected from the group consisting of antibacterials, antifungals, antivirals, and cancer drugs.

7. The process of any one of the preceding clauses wherein the pharmaceutical compound is a cancer drug.

8. The process of any one of the preceding clauses wherein the pharmaceutical compound is docetaxel.

9. The process of any one of clauses 1 to 4 wherein the bioactive compound is an agricultural pesticide selected from the group consisting of insecticides, herbicides, fungicides, and nematicides.

10. The process of any one of the preceding clauses wherein the bioactive compound has a water solubility of about 1 µg/mL to about 500 µg/mL, of about 400 µg/mL to about 300 µg/mL, of about 300 µg/mL to about 200 µg/mL, of about 200 µg/mL to about 100 µg/mL, of about 100 µg/mL to about 50 µg/mL, of about 50 µg/mL to about 25 µg/mL, of about 25 µg/mL to about 10 µg/mL, or of about 10 µg/mL to about 1 µg/mL.

11. The process of any one of the preceding clauses wherein the bioactive compound has a log P value of about 1 to about 2, from about 2 to about 3, from about 3 to about 4, from about 4 to about 5, or from about 5 to about 8.

12. The process of any one of the preceding clauses wherein the amount of the bioactive compound in the solution of (a) is about 1 part of the bioactive compound to about 100 parts (w/w) of glacial acetic acid, 1 part of the bioactive compound to about 200 parts (w/w) of glacial acetic acid, or 1 part of the bioactive compound to about 300 parts (w/w) of glacial acetic acid.

13. The process of any one of the preceding clauses wherein the amount of the acetate salt in the solution of (a) is about 1 part of the acetate salt to about 12 parts of glacial acetic acid (w/w), 1 part of the acetate salt to about 16 parts of glacial acetic acid (w/w), or 1 part of the acetate salt to about 20 parts of glacial acetic acid (w/w).

14. The process of any one of the preceding clauses where the acetate salt is sodium acetate (NaOAc).

15. The process of any of the preceding clauses wherein the evaporation of step (b) is freeze-drying.

16. A composition comprising a CSD of a compound prepared by the process of any one of the preceding clauses.

17. The composition of the preceding clause wherein the CSD is a CSD of docetaxel.

In another embodiment of the invention an acetate salt based CSD is used to enhance the water solubility of a compound with low water solubility. It is appreciated that water solubility of compounds may vary with pH. As used herein, water solubility of a compound generally means water solubility at about pH 6 to about pH 8, unless otherwise stated.

In another embodiment, the compound in any of the embodiments described herein has a water solubility of about 1 mg/mL to about 500 µg/mL, of about 400 µg/mL to about 300 µg/mL, of about 300 µg/mL to about 200 µg/mL, of about 200 µg/mL to about 100 µg/mL, of about 100 µg/mL to about 50 µg/mL, of about 50 µg/mL to about 25 µg/mL, of about µg/mg/mL to about 10 µg/mL, or of about 10 µg/mL to about 1 µg/mL. Compounds with solubilities in the above ranges may be referred to as compounds with low water solubility.

In another embodiment the acetate salt based CSD is used to enhance the water solubility of a compound with a log P value of about 1 to about 2, from about 2 to about 3, from about 3 to about 4, from about 4 to about 5, or from about 5 to about 8. In any of the embodiments described herein, the compound with low water solubility may be a bioactive compound.

As used herein a bioactive compound is a compound selected from the group consisting of flavoring agents, fragrances, herbicides, fungicides, rodenticides, nematacides, insect repellents, and pharmaceutical agents.

As used herein a pharmaceutical agent is any compound used to diagnose, cure, treat, or prevent disease. Some illustrative examples include, but are not limited to enzyme inhibitors, hormones; antibiotics; antiparasitics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; antiinflammatory substances; stimulants; decongestants; antiemetics; diuretics; antispasmodics; antiasthmatics; anti-Parkinson agents; expectorants; cough suppressants; mucolytics; and imaging compounds.

As used herein an aqueous dispersion is made up of fine particles of a material (which may be a bioactive material) that are uniformly distributed throughout the aqueous portion of the dispersion. Improved aqueous dispersion may refer to improved uniformity of the dispersion, smaller particle size of the material in the dispersion, ease of forming the aqueous dispersion from a solid form of the material, and/or lower levels of aggregation of the fine particle during storage of the dispersion.

In an illustrative example of the invention described herein, the preparation and characterization of a CSD of docetaxel in sodium acetate via a solution in glacial acetic acid is described. It is believed that the method described herein has an advantage for CSD engineering because glacial acetic acid (AA, the solvent used as initial drug dissolution medium) is relatively non-toxic (Johnston and Gaas, 2006) and exhibits a high freezing point (FP) of 16.7° C. (Ngo et al., 2016). The high FP may prevent melting of the solvent during a freeze-drying process.

Sodium acetate (SA), is a well-known hydrotropic and a relatively safe chemical (Babak Minofar et al., 2007; Ngo et al., 2016). Aqueous solutions of SA are United States food and drugs administration (FDA) approved for intravenous (IV) infusion and mainly used to treat acidosis in patients (Ekblad et al., 1985; Neavyn et al., 2013). The normal plasma concentration of sodium is in a range of 137-142 mEq/L (Ackerman, 1990). The liver normally metabolizes acetate into bicarbonate (Neavyn et al., 2013). It is a well-known antibacterial and preservative agent (Frech et al., 1979; Sallam, 2007). SA is also used for taste masking (Sharafi et al., 2013; Zheng and Keeney, 2006). It is highly water-soluble. SA does indeed have a surface active and efflorescent property. These intrinsic properties are used to improve the physio-chemical properties of chitosan nanoparticles (Ngo et al., 2016). Up-to-date, little is known about the unique and intrinsic CSD property of SA for hydrophobic drugs.

Docetaxel (DXT) is a BCS class II (Selvamuthukumar et al., 2012; Shah et al., 2014) drug with a log P=4.1 (Tang et al., 2016) and is a poorly water soluble (Malleswara Reddy et al., 2010). It is used to treat different types of malignancies, especially breast, prostate, lung, head, neck, esophageal, squamous cell, and osteosarcoma cancer (Amat et al., 2003; Zhai et al., 2009). DXT binds to microtubules and prevents their depolymerization (Lyseng-Williamson and Fenton, 2005). Current clinical formulation of DXT has several disadvantages. For example, use of a vehicle known to have some systemic toxicity, i.e. polysorbate (de Weger et al., 2014; Engels et al., 2007; Tan et al., 2012). Also use of a solvent such as alcohol which can induce patient intoxication (Mirza and Mithal, 2011). It is herein disclosed that a crystalline solid dispersion of DXT (C-DXT) in SA crystal can be prepared by dispersing native DXT in a SA crystal matrix to reduce and prevent regrowth of DXT crystal size, enhance DXT dissolution rate, resulting in enhanced DXT bioavailability, activity and safety. Supporting physicochemical characterization of the C-DXT formulation (e.g. powder X-ray analysis (PXRD), differential scanning calorimetry (DSC), scanning electron calorimetry (SEM), transmission electron microscopic (TEM), quartz crystal microbalance with dissipation monitoring (QCM-D), dynamic light scattering (DLS), and liquid chromatography tandem mass spectrometry (LC-MS/MS) are provide. The C-DXT formulation cytotoxicity on normal cells (MCF-10A), and disease cells (MCF-7 and MDA-MB468) is assessed by MTS assay.

The disclosure of the foregoing is incorporated herein in its entirety by reference. In addition, the entirety the disclosure of each of the publications cited herein are also incorporated herein by reference.

The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

Abbreviations: AA, glacial acetic acid; APCC, amorphous precipitation in a crystalline carrier; ASD, amorphous solid dispersion; C-DXT, crystal solid dispersion of docetaxel in SA; BCS, biopharmaceutics classification system; CSD, crystal solid dispersion; CSS, crystalline solid solution; DLS, dynamic light scattering; DMEM, Dulbecco modified eagle medium; DSC, differential scanning calorimetry; DXT, docetaxel; IV, intravenous; LC-MS/MS, liquid chromatography tandem mass spectrometry; PXRD, powder X-ray analysis; QCM-D, quartz crystal microbalance with dissipation monitoring; SA, sodium acetate; SAA, sodium acetate anhydrous; SAT, sodium acetate trihydrate; SEM, scanning electron microscopy; TEM, transmission electron microscopy Material Docetaxel (DXT) is purchased from LC Laboratory (Woburn, Mass.). Sodium acetate (SA) anhydrous, Dulbecco modified eagle medium (DMEM) high glucose, DMEM/F12, Non-Essential Amino acid (NEAA), L-glutamine, cholera toxin, hydrocortisone, tween 80, acetonitrile, and formic acid are purchased from Sigma Aldrich (Saint Louis, Mo., USA). Glacial acetic acid (AA) (99.7% w/w), bovine insulin are purchased from Fisher Scientific (Pittsburgh, Pa., USA). Fetal bovine serum (FBS) is obtained from Alphabioregen (Boston, Mass., USA). Penicillin-streptomycin (Pen-Strep) solution is obtained from Invitrogen (Carlsbad, Calif., USA). Horse serum, recombinant human Epidermal Growth Factor (EGF) are purchased from life technologies (Grand island, NY, USA). Rotometals, (San Leandro, Calif., USA), supplies indium. Polyethylene glycol 300 MW (PEG300) and ethanol are obtained from Medisca (Plattsburgh, N.Y., USA).

MCF-7 (human breast adenocarcinoma) estrogen positive, MDAMB-468 (human breast adenocarcinoma) triple negative, MCF10A (cell line mammary normal gland/breast) are purchased from ATCC (Manassas, Va., USA). "Blank SA" is used as a control (not sodium acetate anhydrous) in all the physicochemical characterization analysis. It is the resulting freeze-dried product of sodium acetate anhydrous initially dissolved in AA without DXT. It consists of sodium acetate anhydrous (SAA) and sodium acetate trihydrate (SAT) due to the hygroscopic nature of AA (Doles et al., 2015) and traces of water (0.1% v/v max) in commercially available AA during the dissolution steps of native DXT in AA (Doles et al., 2015). All other chemicals used in this study are of analytical grade and used as received without further purification.

Preparation of Crystal Docetaxel Formulations

The C-DXT formulation engineering process is adjusted from the published method of coating chitosan nanoparticles with SA with a slight modification (Ngo et al., 2016). After a thorough screening related to the media needed to initially dissolve native DXT prior efficient freeze drying and considering the hydrophobic nature of native DXT and its tendency to not dissolve in an aqueous media, the following unique and three-steps process is used to engineer C-DXT:

Firstly, approximately 454 mg of SA anhydrous is dissolved in 8 mL of glacial acetic acid (AA) containing a freshly cleaned beaker with deionized water without vacuum or heat drying for 30 min to generate sodium cation and acetate anion. In fact, in this medium, there is negligible proton transfer from acetic acid to acetate anion due to the weak acidic nature of glacial acetic acid solution with a pKa value of approximately 4.76 (van Beilen et al., 2014).

Secondly, DXT (32 mg) is dissolved in the resulting (AA/SA) solution for 10 min under continuous magnetic stirring. The drug containing (AA/SA) solution is colorless suggesting the complete dissolution of DXT.

Figure 1:
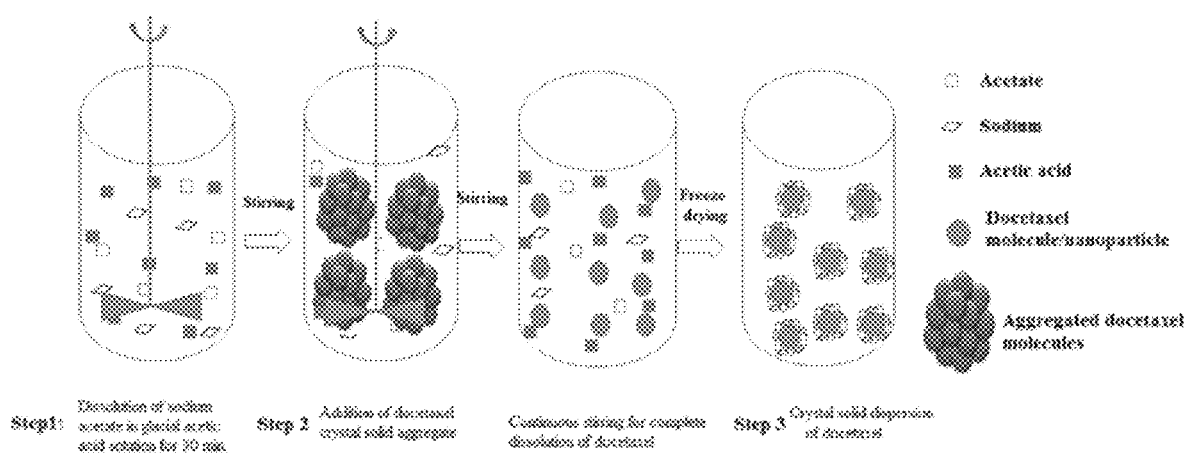
FIG. 1. A schematic for the process of preparation of crystal solid dispersion of docetaxel in sodium acetate crystal FIG. 2. DSC curve of crystal solid dispersion of docetaxel formulation (C-DXT) (a), physical mixture of DXT and blank sodium acetate (SA) (b), blank (SA, Blank SA is obtained by dissolving sodium acetate anhydrous in glacial acetic acid and subsequently freeze-dried) (c), native DXT (d), and indium (e).

Thirdly, DXT solution is frozen using liquid nitrogen and subsequently freeze-dried for 24 h using the benchtop freeze-dryer (Labconco Corporation, Kansas City, Mo., USA). The freeze drying operating conditions are (P~0.06 mBar, T=−48° C.). The freeze-dried product is the C-DXT formulation. The schematic representation of the preparation of C-DXT is shown in FIG. 1.

2.3. Differential Scanning Calorimetry (DSC)

The DSC scan is performed to assess the CSD nature of the DXT dispersed in SA crystals. Briefly, approximately 4 mg of sample is added into an aluminum Tzero pan, sealed with a Tzero lid, and inserted in the left sample pan holder while the reference (empty) is placed into the right sample pan holder. The measurements are performed in a temperature range from 20° C. to 350° C. at a heating rate of 10° C./min under a continuous flow of liquid nitrogen using a Differential Scanning calorimetry 8000 (PerkinElmer, Shelton, Conn., USA). The thermal analysis is performed using Pyris series software (PerkinElmer, Shelton, and Ct). The enthalpy of fusion of samples are calculated using indium with known enthalpy of fusion as a reference (Archer and Rudtsch, 2003).

2.4. X-Ray Powder Diffractometric (XRD)

The XRD analysis is performed to confirm both the regeneration of SA crystal initially dissolved in AA prior to freeze-drying and the inclusion and dispersion of DXT in SA crystal matrix. Briefly, the powder XRD scans are achieved using a MiniFlex automated X-ray diffractometer (Rigaku, The Woodlands, Tex.) at room temperature. Ni-filtered Cu K-alpha radiation is used at 30 kV and 15 mA. The diffraction angle is from $2\theta=5°$ to $2\theta=60°$ with a step size of 0.05°/step, and a count time of 2.5 s/step (effectively 1.1°/min for approximately 46 min/scan). The diffraction patterns are processed using Jade 8+ software (Materials Data, Inc., Livermore, Calif.) (Ngo et al., 2016).

Liquid Chromatography (LC)-Tandem Mass Spectrometry (MS/MS)

The LC-MS/MS analysis is performed to confirm the chemical stability of DXT dispersed in SA crystals (Mortier et al., 2005). SA adduct is used to quantitate DXT (Jones and Denbigh, 2012; Mortier et al., 2005). Briefly, C-DXT formulation (10 μM of DXT) is dissolved in a (49.95/49.95/0.1)% by volume of water/acetonitrile/formic acid, respectively. The control (10 μM of native DXT) is dissolved in an aliquot of the above organic solvent containing spike of blank SA considering the amount of SA in the C-DXT formulation. Mass spectrometry parameter optimization for multiple reaction monitoring (MRM) detection and quantification is achieved using preparative HPLC-purified samples. Detection optimization is achieved using the automated quantitative optimization routine in Analyst version 1.6 (AB SCIEX, Redwood, City, Calif., USA). The separation conditions, the MS conditions and the optimal parameters for the selected precursor/product ion pairs for DXT respectively are shown in Table 1.

TABLE 1

LC-MS/MS conditions for docetaxel qualitative analysis.
Separation conditions

| Instrumentations | HPLC system |
| --- | --- |
| Column | C8 |
| Mobile phase A | 100% Water + 0.1% Formic acid |
| Mobile Phase B | 30% Water + 70% Acetonitrile with 0.1% Formic acid |
| Mobile phase C | 100% Acetonitrile + 0.1% Formic Acid |

| Gradient | Time(min) | Mobile Phase A (% v/v) | Mobile Phase C (% v/v) |
| --- | --- | --- | --- |
| | 0.01 | 90 | 10 |
| | 4 | 90 | 10 |
| | 10 | 0 | 100 |
| | 10.5 | 90 | 10 |
| | 14.5 | 90 | 10 |

TABLE 1-continued

LC-MS/MS conditions for docetaxel qualitative analysis.
Separation conditions

| | |
|---|---|
| Flow rate | 300 µL/min |
| Cell temperature | 40° C. |
| Injection volume | 20 µL |
| Injection wash solvent | 25% methanol |
| MS conditions | |
| Instrumentation | Qtrap |
| Ionization condition | ESI |
| Polarity | Positive |
| Scan time (min) | 14 min |
| Compound transitions | |
| Parent | (m/z) 830.26 |
| Products | (m/z) 304.2 |
| Collision energy | (V) 33 |
| Data processing software | Analyst version 1.6 software |
| Retention time | 11.38 min |

Morphological Analysis

Scanning Electron Microscopy (SEM) Size Analysis in Solid Dry State

The SEM is performed to visualize the morphology of both native DXT crystal and C-DXT in solid powder state. Briefly, a small amount of the sample powder is mounted on ½-in. aluminum stubs with double sticky carbon tape and sputter coated (Emitech EMS575SX) with approximately 20 nm thickness of gold-palladium alloy. The sample is then visualized under a FEI/Philips XL30 Field-Emission Environmental SEM (Philips/FEI, Eindhoven, Netherlands) at 5 kV. Digital images are acquired with ORIUS™ SC 100 large format (II Megapixel) CCD camera (Gatan, Pleasanton, Calif., USA). The length and width range of drugs crystal, C-DXT and control SA in the SEM images are assessed using Image Pro Plus software (Image Pro plus 6.0, Media Cybernetics, Silver Spring, Md., USA) (Meng et al., 2017).

Transmission Electron Microscopy (Tem), Size Analysis of C-DXT Suspension

The TEM is performed to elucidate the surface morphology and the structural information of C-DXT. To get the specimens, the drops of native DXT and C-DXT aqueous suspensions (within 1 min upon addition of deionized water) are placed on a copper grid with a carbon support film and air dried. The suspensions are viewed under a scanning transmission electron microscope CM12 (FEI, Hillsboro, Oreg., USA) at 80 kV accelerating voltage. Digital images are acquired with an ORIUS™ SC 1000 11 Megapixel CCD camera (Gatan, Pleasanton, Calif., USA) (Ngo et al., 2016).

Particle Mean Diameter of C-DXT Nanosuspension

Briefly, 1 mg of C-DXT containing approximately 65.2 µg of DXT is suspended in 1 mL of de-ionized water. The size of the water dispersible nanosuspension is measured using Dynamic light scattering (Zetasizer Nano ZS, Malvern Instruments Ltd, Worcestershire, UK). The experiment is carried out at 25° C. Samples with Polydispersity index (PDI)<0.05 are considered monodispersed according to the National Institute of Standards (Ngo et al., 2016).

Yield and Drug Loading

The amount of C-DXT dispersed in SA matrix and the yield with respect to DXT amount are determined using UV spectrophotometer (Spectronic Genesys 10 Bio, Thermo Electron Corporation, WI, USA) at a wavelength of 230 nm (Loos et al., 1997) (Zhang et al., 2016). Briefly, 1 mg of C-DXT-SA, forming a nanosuspension in de-ionized water is dissolved in 13% v/v of ethanol/water solution. The percent drug loading (% DL) is calculated as follow:

$$\% \ DL = \frac{\text{Amount of } DXT}{\text{Amount of } (SA + DXT)} \times 100 \quad (1)$$

$$\% \ \text{Yield} = \frac{\text{Experimental amount of } DXT}{\text{Theoretical amount of } DXT} \times 100 \quad (2)$$

The calibration curve of DXT is Y=0.0164X−0.0053 (R2=0.9999). where Y is the absorbance of DXT, X is the concentration of DXT in µg/mL.

Quartz Crystal Microbalance with Dissipation Monitoring (QCM-D)

The structural information of C-DXT formulation in pure de-ionized water are monitored using QCM-D (Buttry and Ward, 1992; Ward and Buttry, 1990). Blank SA made of SAA and SAT, a well-known hydrophilic, highly water-soluble salt is used as control. QCM-D experiments are performed using the Q-Sense Analyzer (previously known as QSense E4 Biolin Scientific Inc., NJ 07652), which allowed simultaneous monitoring of frequency (ΔF) and dissipation (ΔD) changes of four individual sensors. The gold-coated AT-cut quartz crystals (QSX301) with a fundamental resonance frequency of 5 MHz are used for all measurements. The crystals are cleansed before each experiment by soaking in a 5:1:1 mixture of de-ionized water, hydrogen peroxide (30%, Sigma Aldrich), and ammonia (25%, Fisher Scientific) at a temperature of 75° C. for 5 min followed by rinsing with DI water and drying with nitrogen gas. All experiments are carried out at a constant flow rate of 50 µL min$^{-1}$ by means of a peristaltic pump (Ismatec IPC-N) (Weckman et al., 2016). The experimental temperature is maintained at 25° C. In each experiment, the gold-coated sensors are allowed to equilibrate in DI water at 25° C. until a stable values of ΔF (related to the mass of the attached film) and ΔD (related to viscoelasticity, stiffness or rigidity) are achieved. Then C-DXT and Blank SA aqueous solutions are flowed and the changes in ΔF and ΔD are recorded in real time. Finally, the sensors are rinsed with DI water. For any rigid and thin film adsorbed onto the sensor surface, the change or shift in frequency is linearly proportional to the change in mass of the attached film as described by Sauerbrey equation (Karczmarczyk et al., 2017):

$$\Delta f = \frac{-n}{C} \Delta m \quad (3)$$

where the number of harmonics (oscillations) at which the crystal is driven or "n"=overtone number (n=1, 3, 5, 7, etc. . . . ) and C=mass sensitivity constant (C=17.7 ng cm$^{-2}$ Hz$^{-1}$ for n=1 or a 5 MHz AT-cut quartz crystal at room temperature). The dissipation factor D (sum of all energy lost in the system) is defined as the inverse of the crystal's quality factor Q as described by the following equation (Bing et al., 2007; Dutta and Belfort, 2007):

$$D = \frac{1}{Q} = \frac{E_{dissipated}}{2\pi E_{stored}} \quad (4)$$

Where $E_{dissipated}$ is the energy loss during one oscillation period and $E_{stored}$ is the energy stored during one oscillation.

Dissolution Study

The dissolution is performed using a USP dissolution apparatus 2 (Scientific Instruments and Technology Corp., Piscataway, N.J.) in 150 mL of 0.1 N HCl. The paddle speed is set at 100 RPM. Briefly, 46 mg of C-DXT formulation containing 3 mg of DXT along with a control (physical mixture of native DXT~3 mg and blank SA~43 mg) is added to each dissolution vessel. At predetermined time interval, 1 mL of sample was withdrawn and replaced with fresh media. Then, samples were centrifuged at 14,000 rpm for 10 min at 25° C. using a refrigerated microcentrifuge (VWR, Radnor, Pa.). The concentration of the drug in the supernatant is measured at 230 nm using the above UV spectrophotometer. The dissolution profile of native docetaxel and C-DXT formulations are compared using the difference factor (f1) and the similarity factor (f2) expressed below (Diaz et al., 2016):

$$f_1 = \left( \frac{\sum_{t=1}^{n} |R_t - T_t|}{\sum_{t=1}^{n} R_t} \right) * 100 \quad (5)$$

$$f_2 = 50 * \log_{10} \left[ \frac{100}{\sqrt{1 + \frac{\sum_{t=1}^{n} (R_t - T_t)^2}{n}}} \right] \quad (6)$$

where n is the number of time points, Rt is the mean dissolution value for the reference product (e.g. native DXT) and Tt is the mean dissolution value for the test product (e.g. C-DXT formulation). In general, a f1 value less than 15 and a f2 value greater than 50 indicate sameness or equivalence in dissolution profile (Diaz et al., 2016)

Cell Culture and Cell Proliferation Assay

Cells and Culture Medium

MCF-7 (human breast adenocarcinoma) Estrogen positive cells are grown in DMEM high glucose supplemented with 10% Fetal Bovine serum (FBS), 10 µg/mL insulin, 1% v/v L-glutamine, 1% v/v penicillin-streptomycin (Pen-Strep) solution and, 1% v/v non-essential amino acid (NEAA). MDA-MB-468 (human breast adenocarcinoma) triple negative cells are grown in DMEM high glucose supplemented with 20% FBS, 1% v/v Pen-Strep and, 1% v/v L-glutamine. Control MCF-10A (normal gland/mammary cell lines) are grown in DMEM/F12 supplemented with 5% v/v Horse serum, 20 ng/mL EGF, 0.5 µg/mL of hydrocortisone, 100 ng/mL of cholera toxin, and 1% v/v pen-strep. Cells are grown and maintained in a monolayer culture, in 75 cm$^2$ culture flasks (Techno Plastic Product, Switzerland), at 37° C. in a humidified atmosphere of 5% carbon dioxide ($CO_2$) (Kulkarni et al., 2017).

Exposure Protocol

C-DXT and simulated clinical DXT formulations, nanosuspension and micellar suspension respectively (Naguib et al., 2014) are added in DMEM high glucose/FBS (10%) or DMEM/F12/Horse Serum (5%) at 65,800 ng/mL and sterilized for 30 min under UV light (Ngo et al., 2016). Different C-DXT and simulated DXT formulations concentration are prepared from the stock solutions 7 mg/mL (solvent=(50/50)% v/v water/PEG) and 20 mg/ml (solvent=(50/50)% v/v (ethanol/tween 80) (Mirza and Mithal, 2011), respectively. Then, the formulations are diluted 1:100; 1:10,000; 1:1,000,000; and 1:100,000,000. MDA-MB-468, MCF-7 (1×10$^4$ cells/100 µL/well) (Garg et al., 2016; Garg et al., 2017), and MCF-10A (1×105 cells/100 pt/well) (Nikkhah et al., 2011; Qu et al., 2015) are seeded in 96 well plate and incubated overnight. The cells are exposed to the C-DXT and simulated clinical DXT at, 0.000658 ng/mL; 0.0658 ng/mL; 6.58 ng/mL; 658 ng/mL; and 65,800 ng/mL for 24 h and 48 h, respectively. Wells containing cells with the culture media only are used as the negative controls. As a positive control, the cells are treated with triton X (1% v/v).

Viable Cell Proliferation Assay

Cell proliferation level is determined by MTS assay. Viable cells bio-reduce MTS compound mix with PMS (cellTiter 96® AQueous) into formazan (Owen, 1993). After exposure to DXT/blank formulations, the old media containing cells is discarded, replaced with 100 µL of fresh media, and equilibrated for 30 min at 37° C. Then, 20 µL cellTiter 96® AQueous (Promega, Madison, Wis., USA) is added to each well and incubated for 1 h. The absorbance is read at 450 nm using a DTX 880 multimode microplate reader (Beckman Coulter, Brea, Calif., USA).

$$\text{Viability} (\%) = \frac{\text{absorbance (test)}}{\text{absorbance (control)}} \times 100 \quad (7)$$

where absorbance (test) and absorbance (control) denote the amount of formazan.

Statistical Analysis

All values are expressed as mean±standard deviations. One-way analysis of variance (ANOVA) in combination with Dunnett's post hoc test are used to compare samples with unequal variances (Duneet, 1980) and identify means of data that are significantly different from each other. A student t-test is used to compare the experimental to the theoretical yield. All statistical analyses are carried out using JMP software version 9, (SAS Institute, Cary, and North Carolina, USA). P-value below 0.05 is considered statistically significant and warrants the rejection of the null hypothesis.

Results

Differential Scanning Calorimetry (DSC)

Figure 2:
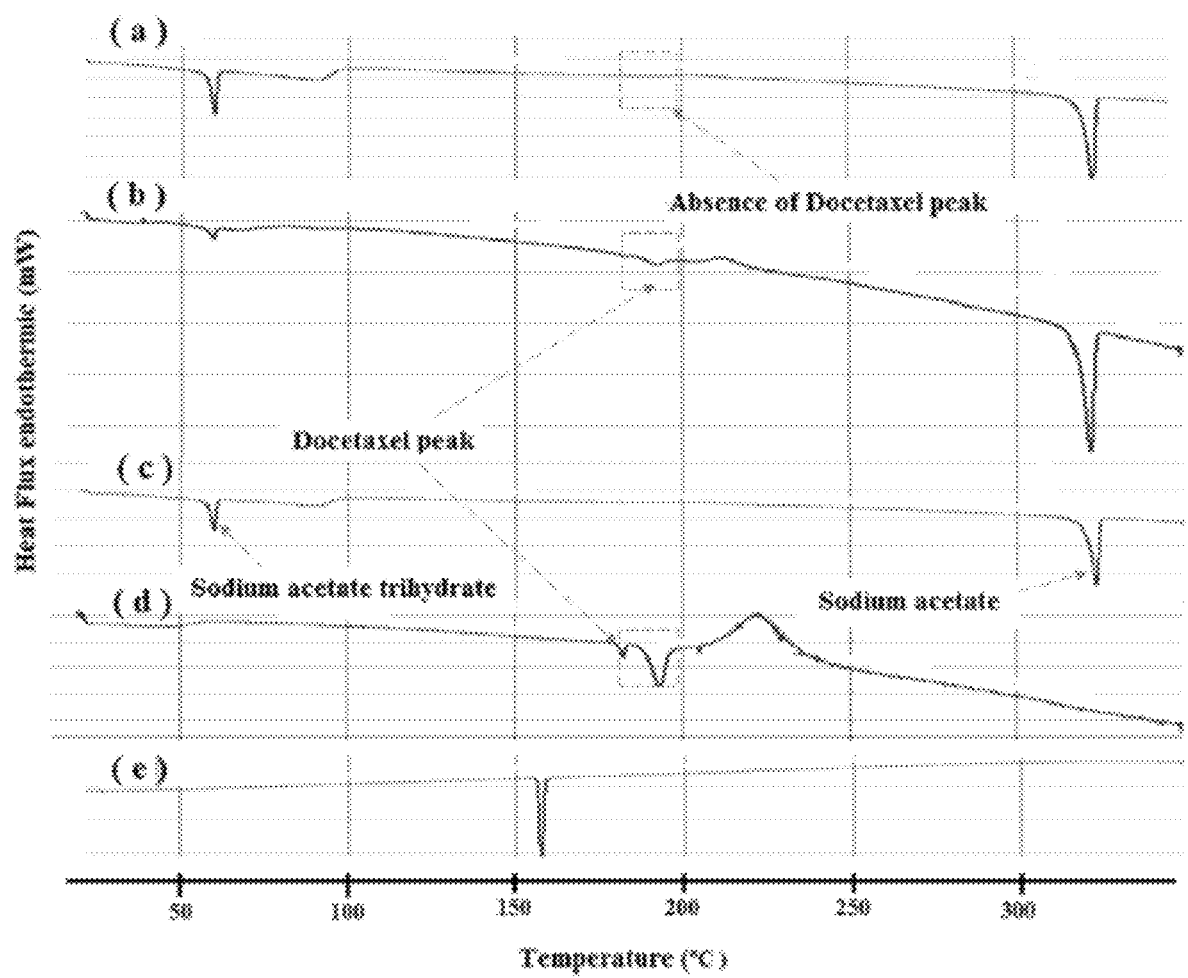

FIG. 2 shows the heat flow curve versus temperature of C-DXT (a), physical mixture of native DXT (32 mg) and blank SA (454 mg) (b), blank SA (c), native DXT (d), and indium (e). The endothermic melting peak of docetaxel is both visible in the native DXT drug FIG. 2d as well as the physical mixture of blank SA and native DXT FIG. 2b, whereas, it disappears in the C-DXT formulation FIG. 2a. The DSC curve of C-DXT and blank SA are alike as shown in FIGS. 2a and c, respectively. These data suggest that DXT is dispersed in blank SA and may be coated with blank SA. Blank SA is made of SAA and SAT as shown in FIG. 2c.
X-Ray Powder Diffractometric (P-XRD)

Figure 3:
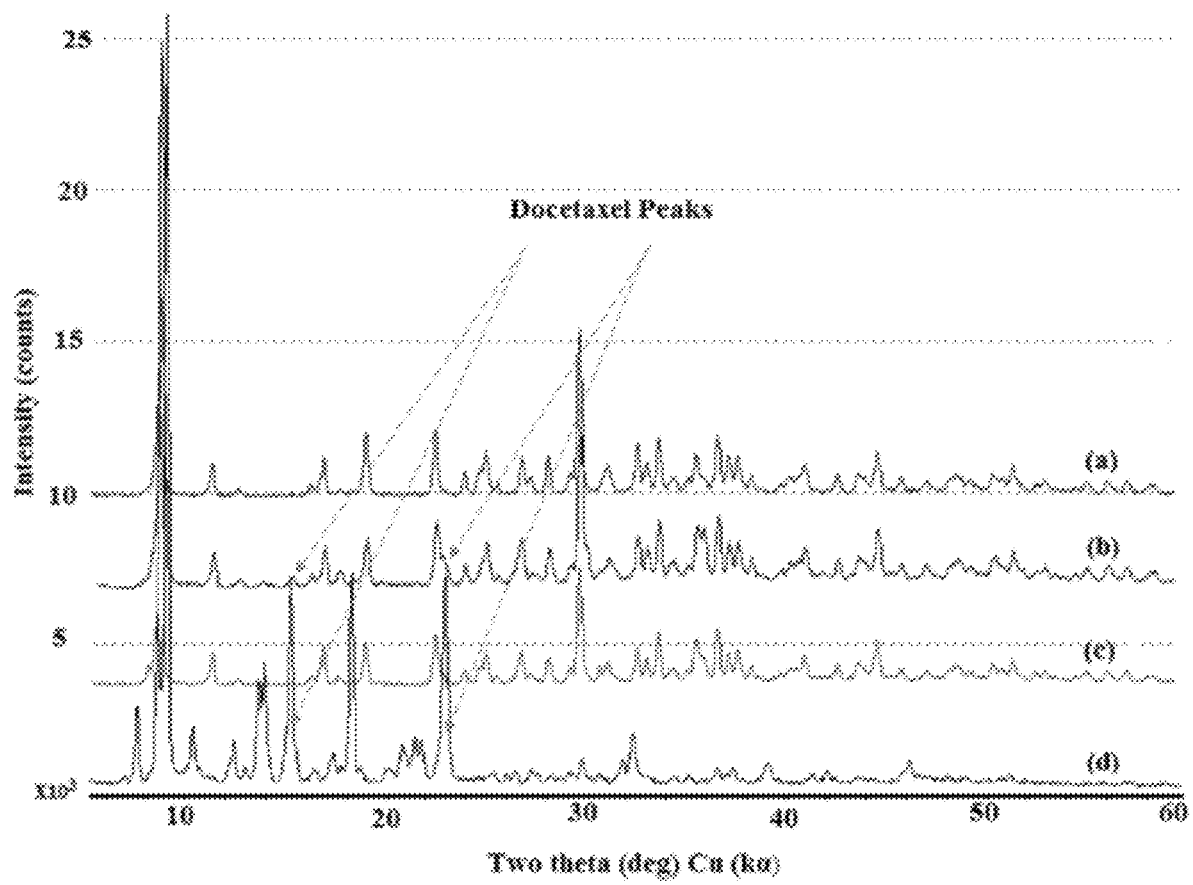
FIG. 3. P-XRD pattern of crystal solid dispersion of docetaxel (C-DXT) (a), physical mixture of DXT and blank SA (b), blank SA (c), and native DXT (d), respectively.

FIG. 3 shows the P-XRD pattern of C-DXT (a), physical mixture of native DXT (32 mg) and SA (454 mg) (b), blank SA (c), and native DXT (d), respectively. The characteristic peaks of DXT at 2 Braggs angle (2θ) equal 15.31° C. and 23.04° C., respectively are present in the physical mixture FIG. 3b and native DXT FIG. 3d (L. Zaske et al., 2001). These DXT characteristics peaks disappear in the C-DXT formulation, as shown in FIG. 3a because DXT may be coated with blank SA and is also dispersed in blank SA (Ngo et al., 2016).

Liquid Chromatography (LC)-Tandem Mass Spectrometry (MS/MS)

Figure 4:
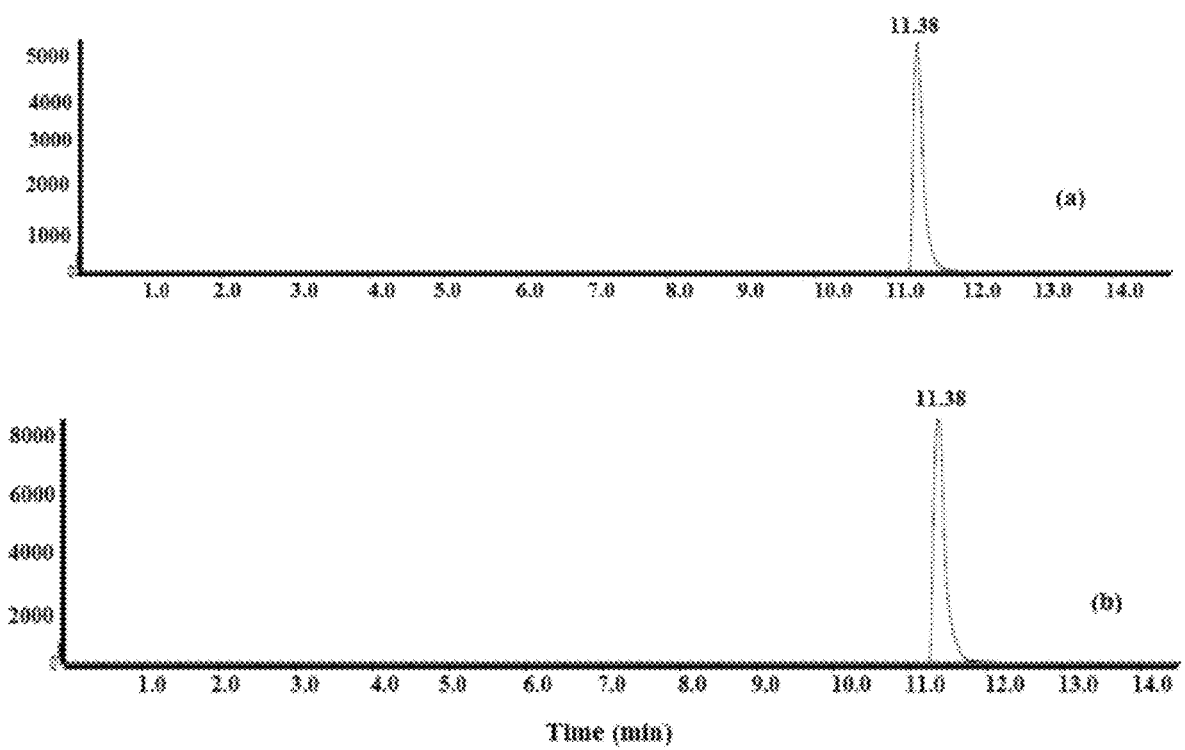
FIG. 4. Chromatogram of native docetaxel (a) and crystal solid dispersion of docetaxel (C-DXT) (b), using multiple reaction monitoring (MRM). Vertical scale is relative intensity (cps)

FIG. 4 shows the chromatogram of native DXT (a) and C-DXT (b) with identical retention time (11.38 min). This suggests that the engineered CSD technique preserves the chemical stability of DXT. The result is indeed expected because DXT is stable in AA solution (Palepu, 2011).

Morphological Analysis: Scanning Electron Microscopy (SEM) and Transmission Electron Microscopy (TEM)

Figure 5:
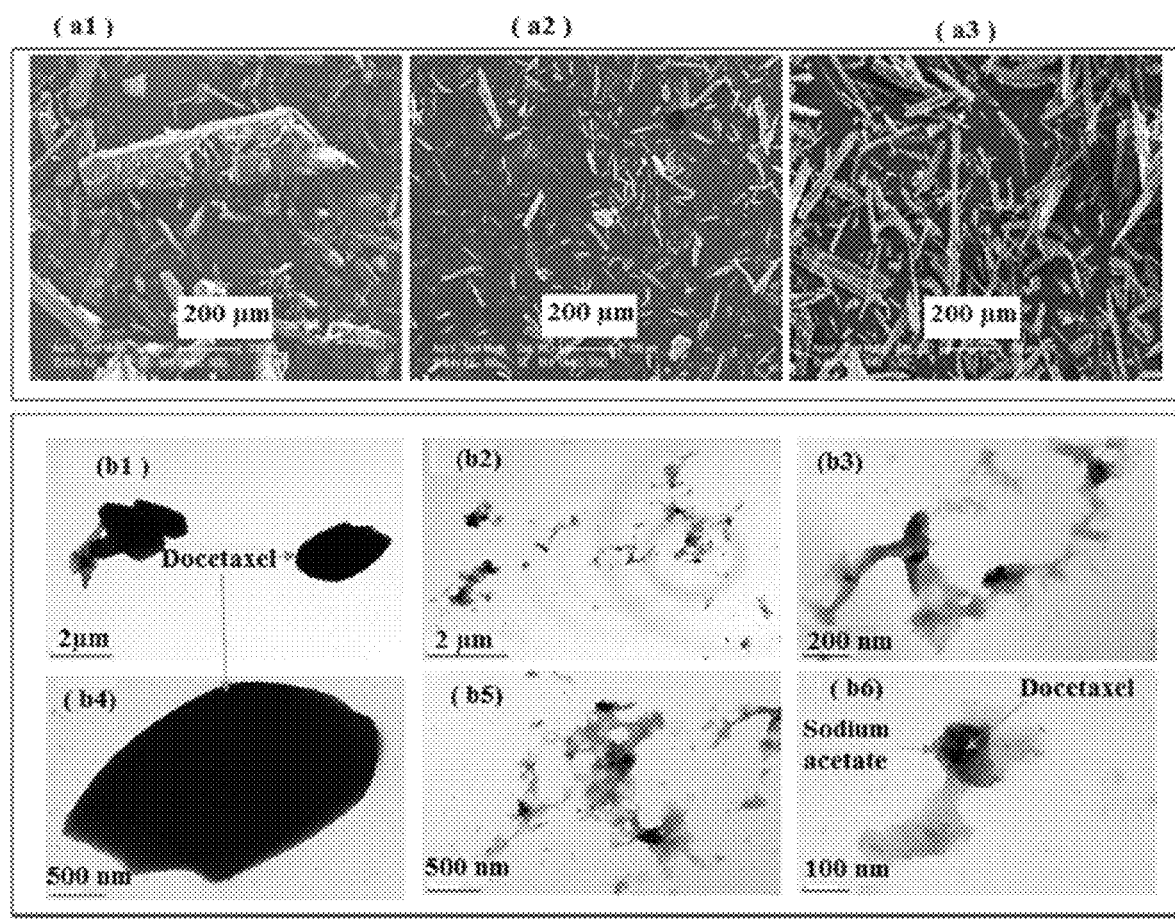
FIG. 5. Scanning electron microscopy (SEM) morphological analysis of native DXT in freeze dried state (a1), blank SA (a2), crystal solid dispersion of docetaxel (CDXT) (a3), respectively in dry powder solid state; Transmission electron microscopy (TEM) aqueous solution of native docetaxel (b1, b4), aqueous solution of crystal solid dispersion of docetaxel (C-DXT) (b2, b3, b5 and b6). A sample drop is placed on a copper grid with a carbon support film and air dried within 1 min. Scale bar represents 200 µm for (a 1-3), 100 nm for (b 6), 200 nm for (b3), 500 nm for (b4, b5), and 2000 nm for (b1, b2) respectively.
Figure 6:
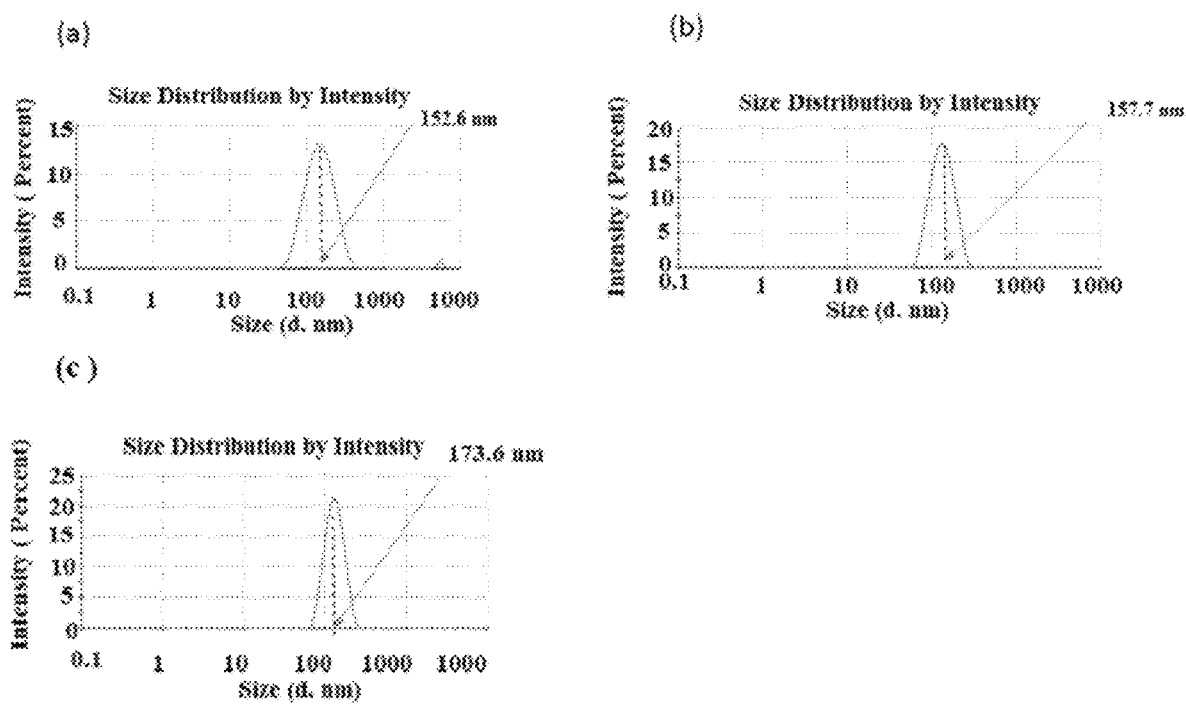
FIG. 6. Particle size distribution of crystal solid dispersion of DXT (C-DXT) in pure deionized water (a-c).

FIG. 5a1-3 shows the SEM morphological analysis of native DXT (FIG. 5a1), blank SA (FIG. 5a2), C-DXT in solid freeze-dried powder state (FIG. 5a3). Unlike native DXT morphology, the morphology of blank SA and C-DXT is identical due to the presence of SA crystals and their surface active property (Ngo et al., 2016). The maximum crystal size is 960.3 µm, 455.2 µm, and 302.8 µm, for native DXT, C-DXT formulation and, blank SA, respectively. FIG. 5b1-6 shows also the TEM morphological and structural analysis of native DXT (FIGS. 5b1 and b4) and C-DXT formulation (FIGS. 5b2, b3, b5 and b6) aqueous suspensions. There is a dramatic decrease of DXT particle size in the C-DXT formulation. Unlike native DXT made of uniform DXT crystal as shown in FIGS. 5b1 and b4, C-DXT nanoparticle (size<200 nm) are made of DXT and blank SA as elucidate by the visual structural information shown in FIG. 5b6. C-DXT presumably contains drug molecules and/or very small drug aggregated coated by SA due to SA surface-active propensity as shown in FIG. 5b6.

Particle Size Distribution, Percent Yield and Drug Loading

In pure deionized water, C-DXT formulation forms a nanosuspension with an average size of approximately 161.3±11 nm as shown in FIG. 6a-c. The percent drug yield is 95.2±4.1%. The experimental and theoretical drug loading are 6.52±0.48% and 6.58%, respectively and are statistically identical based on student t-test analysis with df=2, t=0.22 and p-value=0.58.

Quartz Crystal Microbalance with Dissipation Monitoring (QCM-D)

Figure 7:
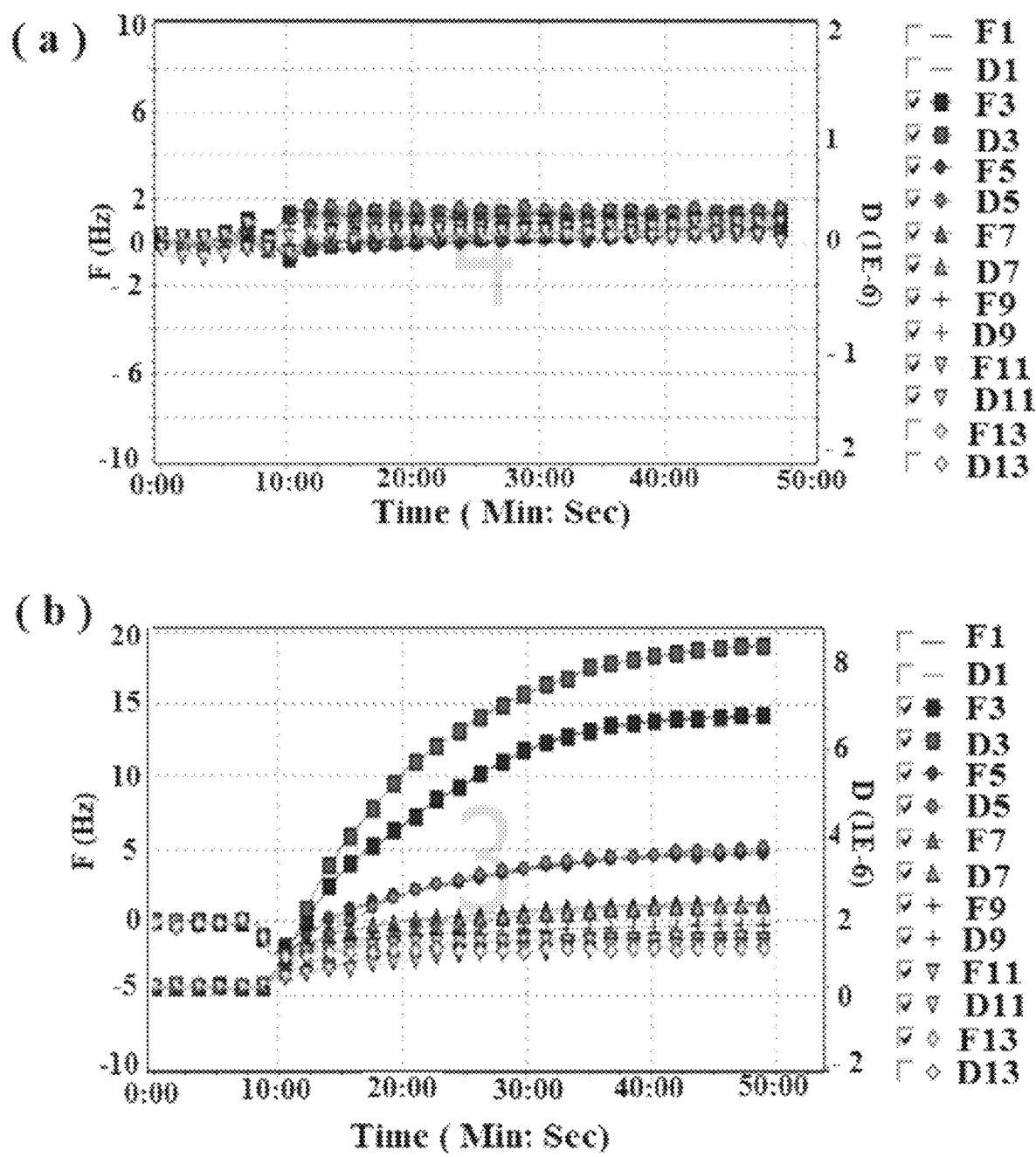
FIG. 7. QCM-D graph of both frequency and dissipation energy versus time of blank SA (a) and crystal solid dispersion of docetaxel (C-DXT) (b), in deionized water. D1 and F1 are the fundamental dissipation and frequency respectively. D3, D5 . . . D11, D13 and F3, F5 . . . F11 and F13 represent the odds overtone for the dissipation and frequency respectively.

FIG. 7 shows the QCM-D graph of both frequency and dissipation values versus time of blank SA (FIG. 7a) and C-DXT (FIG. 7b). The frequency and dissipation of oscillations energies values versus time for blank SA are constant for all n values. These data clearly suggest that there is complete dissolution of SA in deionized water, as expected. The formation of soft or viscoelastic films cause dissipation of oscillation energy (for same n value, D value increases for C-DXT compared to blank SA) due to mechanical losses in the flexible mass (Buttry and Ward, 1992) as shown in FIG. 7b. These C-DXT molecules do not indeed bind tightly among themselves nor rigidly to the QSX301 crystal surface as evidenced by the increase of both the dissipation factor and the frequency (Buttry and Ward, 1992). D1 and F1 are the fundamental dissipation and frequency (for n=1), respectively. For each of the two samples (blank SA/control vs. C-XDT), D3, D5 . . . D11, D13 and F3, F5 . . . F11 and, F13 represent the graph for the odds overtone (n=3, 5, 7, 9, 11 and 13) for the dissipation and frequency, respectively.

Dissolution Study

Figure 8:
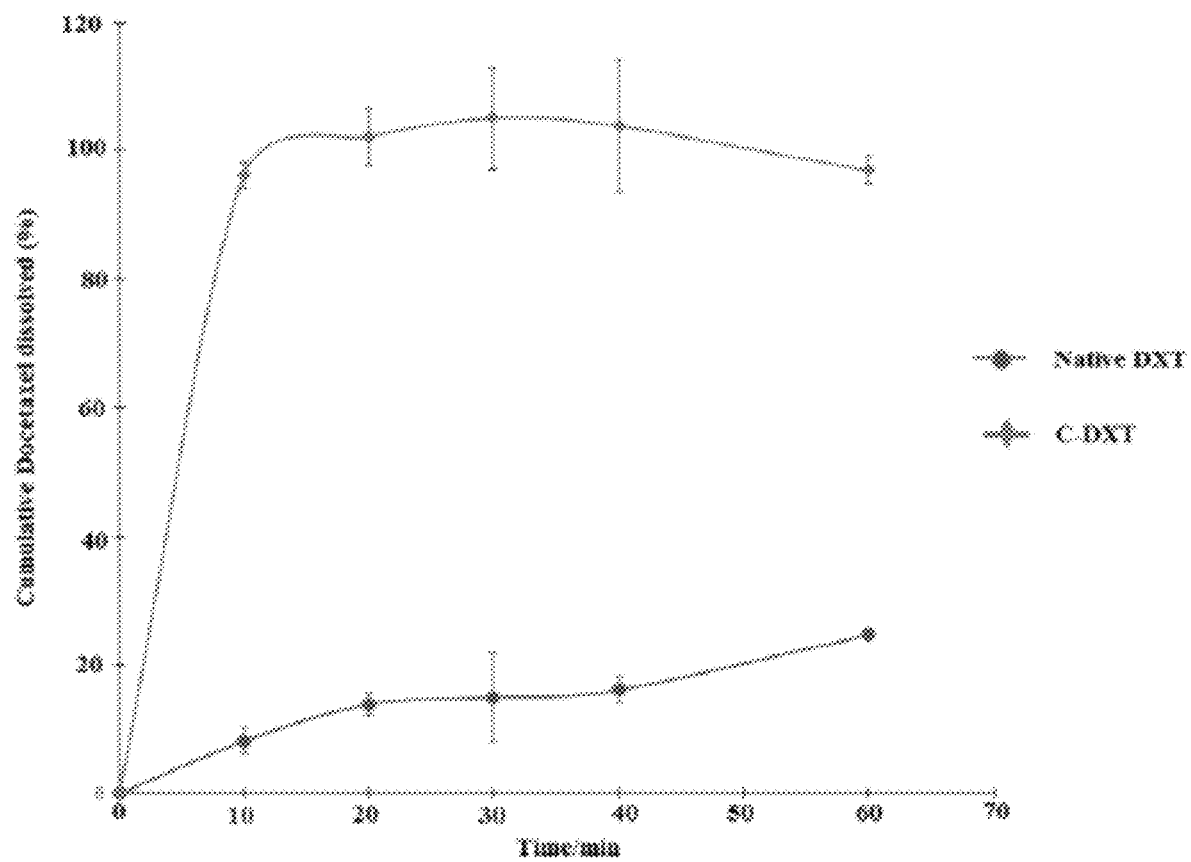
FIG. 8. Dissolution profile of native docetaxel and crystal solid dispersion of docetaxel (C-DXT) in 0.1 N HCl aqueous solution.

FIG. 8 shows the cumulative dissolution profile of C-DXT formulation and native DXT. C-DXT exhibits a fast dissolving profile with 96 percent of the drug dissolved within 10 min. The f1 and f2 values are 547.8 and 7.1 respectively, indicating a non-equivalence of the dissolution profile of C-DXT relatively to native DXT.

Cytotoxicity Assessment

Cytotoxicity Activity on MCF 10A

Figure 9:
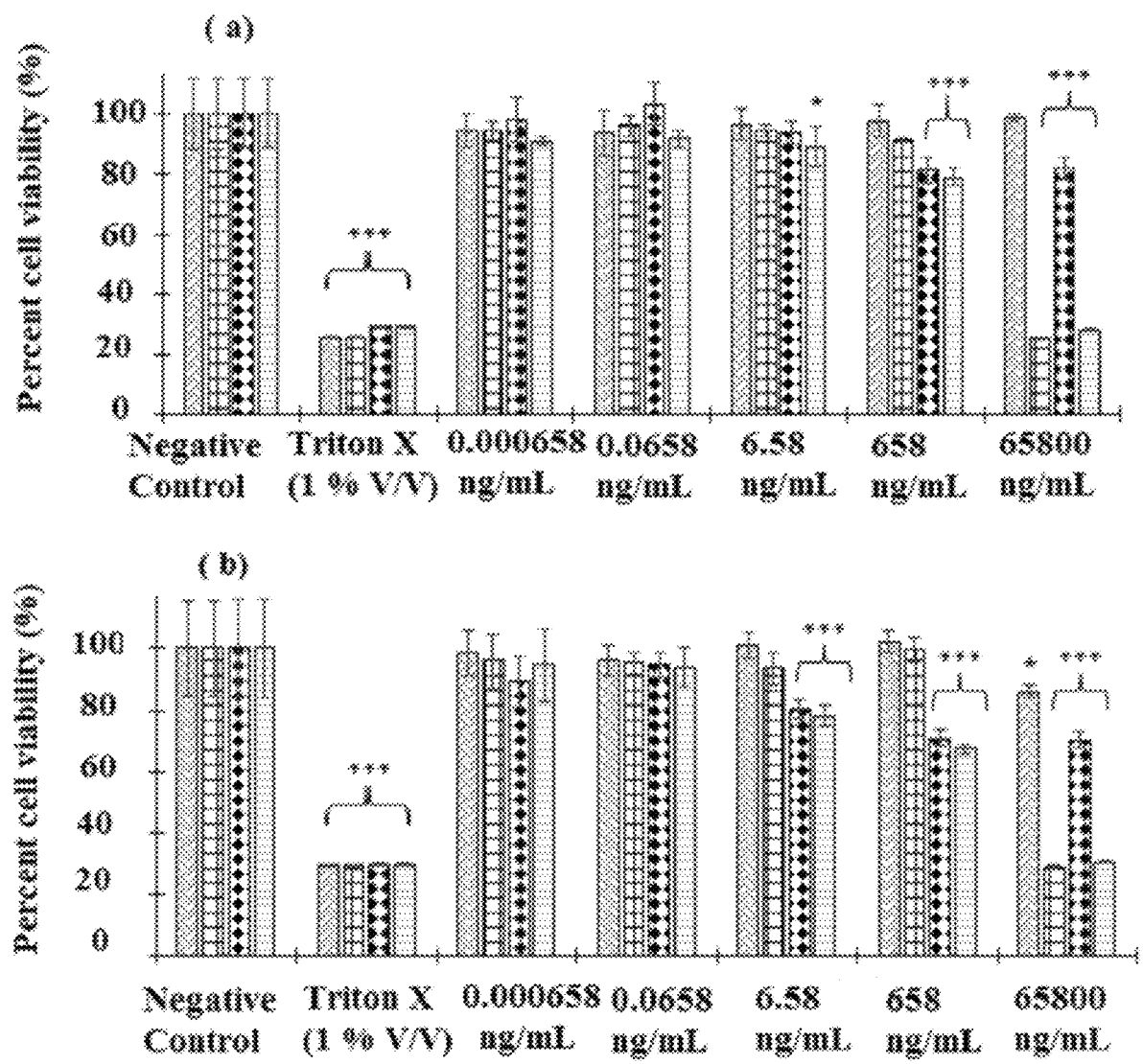
FIG. 9. (a) Percent MCF 10A cell viability (% control) treated 24 h with the different formulations: (from left to right) Blank SA/PEG300 (pattern fill, weave), Blank Tween 80/EtOH (pattern fill, large grid), crystal solid dispersion of docetaxel (C-DXT) (pattern fill, solid diamond grid), and Simulated clinical DXT (pattern fill, Horizontal stripes.

FIG. 9 shows the percent cell viability of MCF 10A after treatment with different formulations. In general, the vehicle, blank SA/PEG300 is safer compared to the blank tween 80/EtOH at highest concentration as shown in FIGS. 9a and b. The cytotoxicity of C-DXT formulation on normal MCF-10A cells is weak over 48 h, whereas a strong cytotoxicity is observed with the simulated clinical formulation DXT as shown in FIG. 9b. The percent cell viability data for simulated clinical DXT formulation (65,800 ng/mL), blank tween 80/EtOH containing both (0.17/0.17%) v/v Tween 80/EtOH are similar and are below 40%. Triton X (1% v/v) is strongly cytotoxic to the cell line as shown in FIG. 9 and is well-known to induces apoptosis and necrotic cell deaths (Borner et al., 1994).

Cytotoxicity Activity on MCF 7 and MDA-MB 468

FIG. 10 shows the percent cell viability of MCF-7. After 24 h of treatments, the cytotoxicity is observed for the highest concentration of C-DXT and simulated clinical DXT formulations, blank SA/PEG300 and the blank Tween 80/EtOH as shown in FIG. 10a. The cytotoxicity of CDXT on MCF-7 increases after 48 h treatment. The blank tween 80/EtOH is also cytotoxic to MCF-7 at (0.17/0.17)% v/v (tween 80/EtOH). The cytotoxicity data of these formulations on MDA-MB-468 cells is shown in FIG. 11. Within 24 h, there is no observed cytotoxicity (FIG. 11a). However, there is an increase of the cytotoxicity when DXT concentration is equal or greater than 6.58 ng/mL as shown in FIG. 11b over a time period of 48 h.

Discussion

The enthalpy of fusion and melting point (MP) of native DXT are 32 J/g and 193.4° C., respectively. Native DXT exhibits endothermic melting peak at 193.4° C. as shown in FIG. 2b in the physical mixture and FIG. 2d. However, there is an absence of the endothermic melting peak of DXT at 193.4° C. on the DSC curve (FIG. 2a) due to both the coating and efflorescent property of SA (Ngo et al., 2016) and the APCC or CSS nature of DXT in SA crystal. The C-DXT formulation is visualized by the SEM and TEM analysis (FIG. 5). The MP of SA in final C-DXT formulation (MP=323.75° C.) (FIG. 2a) is less than that of blank SA (MP=329.06° C.) with respect to SA anhydrous content as shown in FIG. 2c. This result is consistent with Van't Hoff s Law stating that the MP of a pure compound (Blank SA) is always greater than the MP of an impure compound (Kiyo et al., 1998) (C-DXT formulation) (Chiu and Prenner, 2011).

The DSC scans of C-DXT formulation and blank SA are identical as shown in FIGS. 2a and c, respectively. The endothermic melting peak observed at 59.9° C. suggests the formation of SA trihydrate (SAT) crystals during the freeze drying process (FIG. 2a-c) (Green, 1908) due to the hygroscopic nature of AA (Doles et al., 2015) and residual water in commercially available AA (0.1% max) used in the dissolution step of native DXT in AA. The result of this finding is also consistent with the XRD scans. The physical mixture (FIG. 3b) made of blank SA and native DXT show characteristic peaks of DXT at two Braggs angle (2θ) equal 15.31° C. and 23.04° C. whereas, there are no characteristic peaks of DXT at two Braggs angle (2θ) equal 15.31° C. and 23.04° C., shown (FIG. 3a) respectively (Zaske et al., 2001). The PXRD scans of C-DXT and blank SA are identical as shown in FIGS. 3a and c. It is noteworthy that the percent limit of crystallinity detection of the Rigaku Miniflex diffractometer instrument used in this study is in the range of 0.3-1%, which is significantly lower than the actual C-DXT drug loading of 6.52% w/w (Various, 1997). This further supports the fact that DXT (in the C-DXT formulation) is mostly composed of a CSS and/or an APCC of DXT dispersed in blank SA crystalline carrier as visually shown in (FIG. 5b6). When the amorphous drug particles or individual drug molecules are dispersed in a crystalline carrier, the solid dispersion technique is a CSD (Chiou and Riegelman, 1971; Vo et al., 2013). Therefore, the physical state of C-DXT is a CSD of DXT in SA crystal because the carrier "blank SA" is crystalline in nature as evidenced by both the DSC data (FIG. 2C) and the PXRD scan (FIG. 3C), respectively (Baird and Taylor, 2012; Vo et al., 2013). Unlike, the physical mixture of native DXT and SA, the drug/DXT characteristic peaks are absent in both the XRD scan and DSC analysis in the C-DXT formulation. This suggests that the C-DXT formulation or the CSD of DXT in SA carrier is typically composed of an APCC and/or CSS of DXT in SA crystalline carrier (Chiou and Riegelman, 1971). The generation of CSD of DXT may be ascribed to the following physio-chemical properties of glacial acetic acid (AA) and SA.

Firstly, AA and DXT crystals have a good solvation interaction, which is in agreement with Hansen solubility parameters (δHAN). The Hansen solubility parameter (MAN) includes different types of intermolecular forces and is expressed as follow (Hansen, 1967):

$$\delta_{HAN}=\sqrt{\delta_d^2+\delta_p^2+\delta_h^2} \qquad (8)$$

where $\delta_{HAN}$=Hansen solubility parameters, $\delta_d$=energy of dispersions forces between molecules, $\delta_p$=energy of dipolar intermolecular forces between molecules, $\delta_h$=energy of hydrogen bonds between molecules. $\delta_{HAN}$ of AA and DXT are 21.4 (Burke, 1984) and 27.14 (J/cm$^3$)$^{1/2}$, respectively (Huynh et al., 2008). The difference $\Delta\delta_{HAN}$=5.74<7.5 (J/cm$^3$)$^{1/2}$ between DXT ($\delta_{HAN}$) and AA($\delta_{HAN}$) indicates a good solubility of the drug in the selected solvent (Huynh et al., 2008) whereas $\Delta\delta_{HAN}$=20.66>7.5 (J/cm$^3$)$^{1/2}$ between water ($\delta_{HAN}$=47.8 (J/cm$^3$)$^{1/2}$), and DXT ($\delta_{HAN}$) indicates a poor solvation of DXT or solubility (11.75 μg/mL) in deionized-water. This leads to a complete dissolution and surrounding of every single DXT molecule by AA molecules. The stabilization of DXT by the solvation shell formed by AA molecules leads to a colorless solution.

Secondly, DXT molecules are entrapped in AA crystal upon freezing the hygroscopic AA solution (Doles et al., 2015) with liquid nitrogen. In addition, the hydrophobic interaction between solvated DXT molecules is significantly reduced in frozen AA crystal.

Thirdly, in the SA solution prior freeze-drying, Debye-Hükel theory states that species in solution, especially ions of opposite charges, are likely to be found close to each other. Thus, sodium cation and acetate anion are close to each other and surround DXT molecules (Ngo et al., 2016). Moreover, the long-range coulombic interaction between sodium cation and acetate anion leads to the formation of SA. In fact, during the freeze drying process, sodium cation attracts and physically binds to acetate anion through coulombic or charge-charge interaction (Wang et al., 1999). The radii for SA formation, especially the bond length of sodium cation Na+ and oxygen (O) from the carboxylate group COO— is in the range of 2.354-2.56 Å (Cameron et al., 1976). Columbic forces and the free energy for the coulombic interaction between sodium cation and acetate anion can be expressed as:

$$F = \frac{Q_1 Q_2}{4\pi\varepsilon_0 \varepsilon r^2} = \frac{-e^2}{4\pi\varepsilon_0 \varepsilon r} \qquad (9)$$

$$W(r) = \frac{Q_1 Q_2}{4\pi\varepsilon_0 \varepsilon r^2} = \frac{-e^2}{4\pi\varepsilon_0 \varepsilon r} \qquad (10)$$

where F=columbic force; W(r)=free energy for columbic interaction; e=elementary charge 1.602×10$^{-19}$ C; Q1=+e and Q2=−e are sodium cation and acetate anion charges, respectively; r=distance between two isolated sodium cation (Na+) and acetate anion (CH3COO—); ε=relative permittivity or dielectric constant of the medium especially icy or crystal glacial acetic acid, and $\varepsilon_0$=8.85×10-12 C$^2$/Nm$^2$, the vacuum permittivity (Israelachvili, 1991).

In the freeze drying operating condition (0.06 mBar and, 225.15 K) (Ngo et al., 2016), the thermal energy $$kT=(1.38\times10^{-23})(225.15)=3.1\times10^{-21}J. \qquad (11)$$

where the Boltzmann constant, k=1.38×10$^{-23}$ m$^2$ s$^{-2}$ K$^{-1}$.

The dielectric constant (ε) of frozen or crystal acetic acid is 2.5 (Philippe, 1955). Thus, from Eqs. (12) to (13), the value of r must be equal or greater to 297.6 Å (significantly higher than the above bond length) for the coulombic energy to be less than the operating thermal energy kT. This suggests the very long range and strong coulombic interaction between sodium cation and acetate anion during the freezedrying process (Israelachvili, 1991). This resulting strong and long range coulombic force is materialized by the formation of SA.

Fourthly, and most importantly, the surface active and efflorescent properties of SA as demonstrated in our previous study (Babak Minofar et al., 2007; Ngo et al., 2016) not only favor crystal solid dispersion (CSD) of DXT but also the coating of DXT by SA crystal while volatile acetic acid is sublimated (Ngo et al., 2016). The coating and efflorescent property of SA is acetate anion intrinsic amphiphilic property with CH3 the non-polar part oriented at the air solvent interface and COO$^-$ the polar part oriented toward the bulk solution (Babak Minofar et al., 2007; Ngo et al., 2016). Moreover, the removal of the solvent AA by sublimation favors the spontaneous formation and migration of SA salt on the surface of DXT to form a coating layer. This leads to C-DXT formation and distributed in SA crystal. Collectively, the XRD, DSC, and TEM/SEM data, the synergistic effect of the high miscibility between DXT and AA from Hansen solubility parameter, the strong coulombic interaction between sodium cation and acetate anion during the freeze-drying process, the decrease of hydrophobic interaction between DXT molecules in AA and the surface active property of SA explain the underlying physicochemical phenomena governing C-DXT formulation. The CSD of DXT in SA crystal can potentially prevent DXT recrystallization, a common problem inherent to different milling technologies for hydrophobic drugs crystal size reduction (Rabinow, 2004).

The high yield CSD process does not chemically degrade DXT as shown in FIG. 4 because DXT is chemically stable in glacial acetic acid (Palepu, 2011). The retention time of native DXT (FIG. 4a) and native DXT (FIG. 4b) are identical (t=11.38 min).

In pure de-ionized water, C-DXT forms a stable nanosuspension of DXT with a particle mean diameter of 161.3±11 nm for 65.6 µg/mL of DXT as shown in FIG. 6a-c and visualized in FIG. 6d. The nanosuspension exhibit a faster dissolution rate with more than 96.17% of DXT dissolved in 10 min as shown in FIG. 8. This enhanced dissolution rate of C-DXT formulation is due to the synergistic effect of the hydrotropy of blank SA, the coating of DXT by blank SA (Ngo et al., 2016) the APCC and/or CSS nature of DXT in the C-DXT formulation (Chiou and Riegelman, 1971), and the reduction of DXT average particle size (~161.3 nm) in C-DXT formulation. According to, Noyes-Whitney equation as shown below, the decrease of drugs particle size increase their surface area which in turn increase drugs dissolution rate (Chen et al., 2011; Nair, 2016; Koya et al., 2016).

$$\frac{dm}{dt} = A\frac{D}{d}(C_s = C_b), \quad (12)$$

where dm/dt=solute dissolution rate (kg·s$^{-1}$), mass of dissolved material (kg), time ((s), A=surface area of the solute particle (m$^2$)), D=diffusion coefficient (m$^2$/s).

In addition, it is noteworthy that, in this dissolution media, (FIG. 8) the highly water soluble blank SA concentration (~0.0035 M, assuming "blank SA" MW=82.03 g/mol) enables C-DXT rapid dissolution. This effective SA concentration is 571-1143 fold less than the commonly used concentration of SA (2-4M) (Kumar et al., 2013; Vividha Dhapte, 2015) required to enhance the solubility of the hydrophobic drug by hydrotropy. Thus, this unique dual coating and CSD engineering process is extremely crucial to favor not only the rapid dissolution of the CDXT formulation but also maintain DXT concentration above its supersaturation limit in an aqueous media for at least 1 h as shown in (FIG. 8). Indeed, the dissolution of C-DXT formulation is now similar that of the water-soluble carrier blank SA. Furthermore, it is noteworthy that SA (150 mEq or 12.3 g) (Neavyn et al., 2013) and DXT (200 mg) (FDA, 2013) are relatively safe and clinically used for intravenous infusion for acidosis and cancer treatment respectively. For intravenous administration of 200 mg of DXT containing this CSD formulation, in a clinical setting, the required amount of SA would be 2.87 g or 35 mEq which is lower than the clinically used 150 mEq or 12.3 g (Neavyn et al., 2013). It would be 4-fold less SA amount considering drug loading is 6.52% and assuming SA MW=82.03 g/mol suggesting future clinical safety, efficacy and translation feasibility.

For higher concentrations, 1 mg/mL and 7 mg/mL of DXT containing C-DXT formulation can be stabilized in 50/50% v/v deionized water/PEG300 aqueous media for 1 month and 1 h, respectively as shown on FIG. C. This aqueous nanosuspension appears to be non-rigid in nature as revealed by the QCM-D result considering the increase of both frequency and dissipation factor (FIG. 7b) (Buttry and Ward, 1992). It is noteworthy that the nanosuspension size is less than 200 nm and acceptable for IV administration (Merkle et al., 2003).

Based on ISO 10993-5 for in vitro cytotoxicity test with 100% viability allotted to the control, samples cytotoxicity level are classified as not cytotoxic, weak, moderate, and strong for cell viability higher than 80%, within 80-60%, within 60-40%, and strong below 40% respectively (Garle et al., 1994; Ngo et al., 2016). In this study, the blank SA/PEG 300 containing (0.093% w/v SA) and 0.47% v/v PEG 300, respectively appeared to be non-cytotoxic to MCF-10A, whereas the vehicle tween 80/EtOH (0.17/0.17)% v/v strong cytotoxic observed to MCF-10A cells, is mainly due to ethanol as reported in previous study (Tapani et al., 1996; Tsujino et al., 1999). Compared to other xenobiotics previously used to overcome drug solubility problems, acetate is a very attractive alternative because it is a relatively safer natural bioactive agents involved in normal cell biochemistry during the Krebs cycle (Spencer et al., 1974). In general, the cytotoxicity levels of C-DXT and Simulated clinical DXT formulation on MCF-10A, MCF-7 and MDAMB-468 is dose dependent and increase over a period of 48 h in all cell lines as shown in FIGS. 9, 10 and 11. Below, DXT concentration of 6.85 ng/mL (8.14 nM), both C-DXT and simulated clinical DXT formulation appeared to be non-cytotoxic to the different cell lines. The cytotoxicity of DXT is observed with DXT concentration equal to, or greater than 6.85 ng/mL for both simulated clinical DXT and C-DXT as shown in FIG. 11b. The cytotoxicity observed up to 8.14 nM of DXT concentration is consistent with reported IC50 of DXT, which was 8.2 nM over an exposure time period of 72 in a previous study (Kucukzeybek et al., 2008). These results suggest that DXT nanosuspensions are uptaken by different cell line and the activity of DXT is preserved after the formulation engineering. The formation of a nanosuspension may potentially and selectively accumulate in tumor tissue due the enhanced permeability and retention (EPR) effect (Sumer Bolu et al., 2016; Yhee et al., 2017) and may potentiate the activity and safety of DXT.

CONCLUSIONS

A novel crystal solid dispersion (CSD) of docetaxel (C-DXT) is successfully engineered by molecularly dispersing a model BCS class II drug, DXT in sodium acetate crystal matrix. The proposed CSD engineering process is relatively simple and preserved the drug chemical stability in the C-DXT formulation. In an aqueous media, C-DXT formulation forms a non-rigid nanosuspension exhibiting a faster dissolution kinetics. The physical stability of C-DXT is time and concentration dependent. The cytotoxicity of C-DXT are comparable to that of simulated clinical DXT. At higher dose the vehicle SA/PEG 300 is safer than the vehicle tween 80/ETOH for normal cell. Such drug CSD engineering process using the highly water-soluble salt such as SA as a dispersion medium may be used to prevent recrystallization of hydrophobic drugs (from BCS class II and IV) in solid state, reduce drug crystal size, enhance their aqueous dissolution rate resulting in enhanced bioavailability; and potentiate their safety and efficacy.

While certain embodiments of the present invention have been described and/or exemplified above, it is contemplated that considerable variation and modification thereof are possible. Accordingly, the present invention is not limited to the particular embodiments described and/or exemplified herein.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

REFERENCES

Ackerman, G. L., 1990. Serum Sodium. In: rd, Walker, H. K., Hall, W. D., Hurst, J. W. (Eds.), Clinical Methods: The History, Physical, and Laboratory Examinations. Boston.

Amat, S., Bougnoux, P., Penault-Llorca, F., Fetissof, F., Cure, H., Kwiatkowski, F., Achard, J. L., Body, G., Dauplat, J., Chollet, P., 2003. Neoadjuvant docetaxel for operable breast cancer induces a high pathological response and breast-conservation rate. Br. J. Cancer 88, 1339-1345.

Babak Minofar, P. J., Das, Manash R., Kunz, Werner, Mahiuddin, Sekh, 2007. Propensity of formate, acetate, benzoate, and phenolate for the aqueous solution/vapor interface: surface tension measurements and molecular dynamics simulations. J. Phys. Chem. 111, 8242-8247.

Badal Tejedor, M., Nordgren, N., Schuleit, M., Pazesh, S., Alderborn, G., Millqvist-Fureby, A., Rutland, M. W., 2017. Determination of interfacial amorphicity in functional powders. Langmuir 33, 920-926.

Baird, J. A., Taylor, L. S., 2012. Evaluation of amorphous solid dispersion properties using thermal analysis techniques. Adv. Drug Deliv. Rev. 64, 396-421.

Bing, Wu, Kun, Wu, Wang, Ping, Zhu, Da-Ming, 2007. Adsorption Kinetics and Adsorption Isotherm of Poly(N-isopropylacrylamide) on GoldSurfaces Studied Using QCM-D. J. Phys. Chem. 111, 1131-1135.

Borner, M. M., Schneider, E., Pirnia, F., Sartor, O., Trepel, J. B., Myers, C. E., 1994. The detergent Triton X-100 induces a death pattern in human carcinoma cell lines that resembles cytotoxic lymphocyte-induced apoptosis. FEBS Lett. 353, 129-132. Burke, J., 1984. Solubility Parameters: Theory and Application. The Book and Paper Group, the American Institute for Conservation 3.

Cameron, T. S., Mannan, K. M., Rahman, M. O., 1976. The crystal structure of sodium acetate trihydrate. Acta Crystallogr., B 87-90.

Chen, H., Khemtong, C., Yang, X., Chang, X., Gao, J., 2011. Nanonization strategies for poorly water-soluble drugs. Drug Discov. Today 16, 354-360.

Cheow, W. S., Kiew, T. Y., Yang, Y., Hadinoto, K., 2014. Amorphization strategy affects the stability and supersaturation profile of amorphous drug nanoparticles. Mol. Pharm. 11, 1611-1620.

Chiou, W. L., Riegelman, S., 1971. Pharmaceutical applications of solid dispersion systems. J. Pharm. Sci. 60, 1281-1302.

Chiu, M. H., Prenner, E. J., 2011. Differential scanning calorimetry: An invaluable tool for a detailed thermodynamic characterization of macromolecules and their interactions. J. Pharm. Bioallied Sci. 3, 39-59.

Craig, D. Q., 2002. The mechanisms of drug release from solid dispersions in water-soluble polymers. Int. J. Pharm. 231, 131-144.

Curtin, V., Amharar, Y., Hu, Y., Erxleben, A., McArdle, P., Caron, V., Tajber, L., Corrigan, O. I., Healy, A. M., 2013. Investigation of the capacity of low glass transition temperature excipients to minimize amorphization of sulfadimidine on comilling. Mol. Pharm. 10, 386-396.

Buttry, Daniel A., Ward, M. D., 1992. Measurement of interfacial processes at electrode surfaces with the electrochemical quartz crystal microbalance. Chem. Rev. 92, 1355-1379.

de Weger, V. A., Beijnen, J. H., Schellens, J. H., 2014. Cellular and clinical pharmacology of the taxanes docetaxel and paclitaxel—a review. Anticancer Drugs 25, 488-494.

Diaz, D. A., Colgan, S. T., Langer, C. S., Bandi, N. T., Likar, M. D., Van Alstine, L., 2016. Dissolution similarity requirements: how similar or dissimilar are the global regulatory expectations? AAPS J. 18, 15-22.

Doles, W., Wilkerson, G., Morrison, S., Richmond, R. G., 2015. Glacial acetic acid adverse events: case reports and review of the literature. Hosp. Pharm. 50, 304-309.

Archer, Donald G., Rudtsch, S., 2003. Enthalpy of fusion of indium: a certified reference material for differential scanning calorimetry. J. Chem. Eng. 48, 1157-1163.

Duneet, C. W., 1980. Pairwise multiple comparisons in the unequal variance case. J. Am. Stat. Assoc. 75, 796-800.

Dutta, A. K., Belfort, G., 2007. Adsorbed gels versus brushes: viscoelastic differences. Langmuir 23, 3088-3094.

Ekblad, H., Kero, P., Takala, J., 1985. Slow sodium acetate infusion in the correction of metabolic acidosis in premature infants. Am. J. Dis. Child 139, 708-710.

Engels, F. K., Mathot, R. A., Verweij, J., 2007. Alternative drug formulations of docetaxel: a review. Anticancer Drugs 18, 95-103. FDA, 2013. Taxotere (docetaxel) injection Concentrated, Intravenous Infusion (IV), refence ID: 3421782. FDA, US-Federal Register.

Frech, G., Allen Jr., L. V., Stiles, M. L., Levinson, R. S., 1979. Sodium acetate as a preservative in protein hydrolysate solutions. Am. J. Hosp. Pharm. 36, 1672-1675.

Garg, N. K., Singh, B., Kushwah, V., Tyagi, R. K., Sharma, R., Jain, S., Katare, O. P., 2016. The ligand (s) anchored lipobrid nanoconstruct mediated delivery of methotrexate: an effective approach in breast cancer therapeutics. Nanomedicine 12, 2043-2060.

Garg, N. K., Tyagi, R. K., Sharma, G., Jain, A., Singh, B., Jain, S., Katare, O. P., 2017. Functionalized lipid-polymer hybrid nanoparticles mediated codelivery of methotrexate and aceclofenac: a synergistic effect in breast cancer with improved pharmacokinetics attributes. Mol. Pharm. 14, 1883-1897.

Garle, M. J., Fentem, J. H., Fry, J. R., 1994. In vitro cytotoxicity tests for the prediction of acute toxicity in vivo. Toxicol. In Vitro 8, 1303-1312.

Goncalves, C., Gomez, J. P., Meme, W., Rasolonjatovo, B., Gosset, D., Nedellec, S., Hulin, P., Huin, C., Le Gall, T., Montier, T., Lehn, P., Pichon, C., Guegan, P., Cheradame, H., Midoux, P., 2017. Curcumin/poly(2-methyl-2-oxazoline-b-tetrahydrofuran-b-2-methyl-2-oxazoline) formulation: an improved penetration and biological effect of curcumin in F508del-CFTR cell lines. Eur. J. Pharm. Biopharm.

Green, W. F., 1908. The "Melting-Point" of hydrated sodium acetate: solubility curves. J. Phys. Chem. 12, 655-660.

Hansen, C. M., 1967. The three dimensional solubility parameter and solvent diffusion coefficient, their improtance in surface Coating formulation. Copenhagen Danish Technical Press.

Huynh, L., Grant, J., Leroux, J. C., Delmas, P., Allen, C., 2008. Predicting the solubility of the anti-cancer agent docetaxel in small molecule excipients using computational methods. Pharm. Res. 25, 147-157.

Israelachvili, J. N., 1991. Intermolecular and surface forces, second ed. Academic.

Jones, J., Denbigh, J., 2012. LC-MS/MS Method for the Determinationof Docetaxel in Human Serum for Clinical Research. Thermoscientific chromatography.

Jensen, K. T., Larsen, F. H., Cornett, C., Lobmann, K., Grohganz, H., Rades, T., 2015. Formation mechanism of coamorphous drug-amino acid mixtures. Mol. Pharm. 12, 2484-2492.

Johnston, C. S., Gaas, C. A., 2006. Vinegar: medicinal uses and antiglycemic effect. MedGenMed 8, 61.

Kalepu, S., Nekkanti, V., 2015. Insoluble drug delivery strategies: review of recent advances and business prospects. Acta Pharm. Sin. B 5, 442-453.

Karczmarczyk, A., Haupt, K., Feller, K. H., 2017. Development of a QCM-D biosensor for Ochratoxin A detection in red wine. Talanta 166, 193-197.

Kauppinen, A., Broekhuis, J., Grasmeijer, N., Tonnis, W., Ketolainen, J., Frijlink, H. W., Hinrichs, W. L. J., 2017. Efficient production of solid dispersions by spray drying solutions of high solid content using a 3-fluid nozzle. Eur. J. Pharm. Biopharm.

Kawabata, Y., Yamamoto, K., Debari, K., Onoue, S., Yamada, S., 2010. Novel crystalline solid dispersion of tranilast with high photostability and improved oral bioavailability. Eur. J. Pharm. Sci. 39, 256-262.

Kiyo, Y., Michihiko, M., Seiji, K., Kusuo, N., 1998. Determination of the purity of Multicomponent organic Substacnces by DSC. Anal. Sci. 14, 599-602.

Koya, Y., Uchida, S., Machi, Y., Shobu, Y., Namiki, N., Kotegawa, T., 2016. Prediction of drug interaction between oral adsorbent AST-120 and concomitant drugs based on the in vitro dissolution and in vivo absorption behavior of the drugs. Eur. J. Clin. Pharmacol. 72, 1353-1361.

Kucukzeybek, Y., Gul, M. K., Cengiz, E., Erten, C., Karaca, B., Gorumlu, G., Atmaca, H., Uzunoglu, S., Karabulut, B., Sanli, U. A., Uslu, R., 2008. Enhancement of docetaxelinduced cytotoxicity and apoptosis by all-trans retinoic acid (ATRA) through downregulation of survivin (BIRCS), MCL-1 and LTbeta-R in hormone- and drug resistant prostate cancer cell line, DU-145. J. Exp. Clin. Cancer Res. 27, 37.

Kulkarni, Y. M., Yakisich, J. S., Azad, N., Venkatadri, R., Kaushik, V., O'Doherty, G., Iyer, A. K. V., 2017. Antitumorigenic effects of a novel digitoxin derivative on both estrogen receptor-positive and triple-negative breast cancer cells. Tumour Biol. 39 1010428317705331.

Kumar, V. S., Raja, C., Jayakumar, C., 2013. A review on solubility enhancement using hydrotropic phenomena. Int. J. Pharm. Pharm. Sci. 6, 1-7.

Zaske, L., Perrin, M.-A., Leveiller, F., 2001. Docetaxel: Solid state characterization by Xray powder diffraction and thermogravimetry. J. Phys. IV, 221-226.

LaFountaine, J. S., Prasad, L. K., Miller, D. A., McGinity, J. W., Williams 3rd, R. O., 2017. Mucoadhesive amorphous solid dispersions for sustained release of poorly water soluble drugs. Eur. J. Pharm. Biopharm. 113, 157-167.

Lobmann, K., Laitinen, R., Grohganz, H., Gordon, K. C., Strachan, C., Rades, T., 2011. Coamorphous drug systems: enhanced physical stability and dissolution rate of indomethacin and naproxen. Mol. Pharm. 8, 1919-1928.

Loos, W. J., Verweij, J., Nooter, K., Stoter, G., Sparreboom, A., 1997. Sensitive determination of docetaxel in human plasma by liquid-liquid extraction and reversed-phase high-performance liquid chromatography. J. Chromatogr., B 693, 437-441.

Lyseng-Williamson, K. A., Fenton, C., 2005. Docetaxel: a review of its use in metastatic breast cancer. Drugs 65, 2513-2531.

Malleswara Reddy, A., Banda, N., Govind Dagdu, S., Venugopala Rao, D., Kocherlakota, C. S., Krishnamurthy, V., 2010. Evaluation of the pharmaceutical quality of docetaxel injection using new stability indicating chromatographic methods for assay and impurities. Sci. Pharm. 78, 215-231.

Marano, S., Barker, S. A., Raimi-Abraham, B. T., Missaghi, S., Rajabi-Siahboomi, A., Craig, D. Q. M., 2016. Development of micro-fibrous solid dispersions of poorly water-soluble drugs in sucrose using temperature-controlled centrifugal spinning. Eur. J. Pharm. Biopharm. 103, 84-94.

Martinez, L. M., Videa, M., Lopez Silva, T., Castro, S., Caballero, A., Lara-Diaz, V. J., Castorena-Torres, F., 2017. Two-phase amorphous-amorphous solid drug dispersion with enhanced stability, solubility and bioavailability resulting from ultrasonic dispersion of an immiscible system. Eur. J. Pharm. Biopharm. 119, 243-252.

Meng, J., Agrahari, V., Ezoulin, M. J., Purohit, S. S., Zhang, T., Molteni, A., Dim, D., Oyler, N. A., Youan, B. C., 2017. Spray-dried thiolated chitosan-coated sodium alginate multilayer microparticles for vaginal HIV microbicide delivery. AAPS J. 19, 692-702.

Merkle, F., Bottcher, W., Hetzer, R., 2003. Prebypass filtration of cardiopulmonary bypass circuits: an outdated technique? Perfusion 18 (Suppl. 1), 81-88.

Mirza, A., Mithal, N., 2011. Alcohol intoxication with the new formulation of docetaxel. Clin. Oncol. 23, 560-561.

Mortier, K. A., Renard, V., Verstraete, A. G., Van Gussem, A., Van Belle, S., Lambert, W. E., 2005. Development and validation of a liquid chromatography-tandem mass spectrometry assay for the quantification of docetaxel and paclitaxel in human plasma and oral fluid. Anal. Chem. 77, 4677-4683.

Naguib, Y. W., Rodriguez, B. L., Li, X., Hursting, S. D., Williams 3rd, R. O., Cui, Z., 2014. Solid lipid nanoparticle formulations of docetaxel prepared with high melting point triglycerides: in vitro and in vivo evaluation. Mol. Pharm. 11, 1239-1249.

Nair, S. S. A. R., 2016. Methods of nanonization of drugs for enhancing their dissolution. Eur. J. Adv. Eng. Technol. 3, 101-110.

Neavyn, M. J., Boyer, E. W., Bird, S. B., Babu, K. M., 2013. Sodium acetate as a replacement for sodium bicarbonate in medical toxicology: a review. J. Med. Toxicol. 9, 250-254.

Ngo, A. N., Ezoulin, M. J., Murowchick, J. B., Gounev, A. D., Youan, B. B., 2016. Sodium acetate coated tenofovir-loaded chitosan nanoparticles for improved physicochemical properties. Pharm. Res. 33, 367-383.

Ngo, A. N., Youan, B. B. C., 2016. Formulations for pharmaceutical agents US 20160361327 A1. U.S. patent application No. 62/173,772.

Nikkhah, M., Strobl, J. S., Schmelz, E. M., Roberts, P. C., Zhou, H., Agah, M., 2011. MCF10 Å and MDA-MB-231 human breast basal epithelial cell co-culture in silicon micro-arrays. Biomaterials 32, 7625-7632.

Owen, T. C., 1993. Tetrazolium compound for cell viability assays. U.S. Pat. No. 5,185,450A.

Palepu, N. R., 2011. Docetaxel formulations with lipoic acid. US patent #US 20120129922 A1.

Philippe, R. P. A. M., 1955. Recherches de Stoechiométrie VII(1) Contribution à l'étude de la constante diélectrique des composes organiques purs. Bull. Soc. Chim. Belges 64, 600-627.

Qu, Y., Han, B., Yu, Y., Yao, W., Bose, S., Karlan, B. Y., Giuliano, A. E., Cui, X., 2015. Evaluation of MCF10 Å as a reliable model for normal human mammary epithelial cells. PLoS One 10, e0131285.

Rabinow, B. E., 2004. Nanosuspensions in drug delivery. Nat. Rev. Drug Discov. 3, 785-796.

Saal, W., Ross, A., Wyttenbach, N., Alsenz, J., Kuentz, M., 2017. A systematic study of molecular interactions of anionic drugs with a dimethylaminoethyl methacrylate copolymer regarding solubility enhancement. Mol. Pharm. 14, 1243-1250.

Sallam, K. I., 2007. Antimicrobial and antioxidant effects of sodium acetate, sodium lactate, and sodium citrate in refrigerated sliced salmon. Food Control 18, 566-575.

Selvamuthukumar, S., Anandam, S., Kalman, K., Manavalan, R., 2012. Nanosponges: a novel class of drug delivery system-review. J. Pharm. Pharm. Sci. 15, 103-111.

Shah, S. M., Jain, A. S., Kaushik, R., Nagarsenker, M. S., Nerurkar, M. J., 2014. Preclinical formulations: insight, strategies, and practical considerations. AAPS PharmSciTech 15, 1307-1323.

Sharafi, M., Hayes, J. E., Duffy, V. B., 2013. Masking vegetable bitterness to improve palatability depends on vegetable type and taste phenotype. Chemosensory Perception 6, 8-19.

Spencer, E. K., Ivan, G. J., Owen, H. F., Ballard, F. J., 1974. Production and utilization of acetate in mammals. Biochem. J. 142, 401-411.

Sumer Bolu, B., Manavoglu Gecici, E., Sanyal, R., 2016. Combretastatin A-4 conjugated antiangiogenic micellar drug delivery systems using dendron-polymer conjugates. Mol. Pharm. 13, 1482-1490.

Tan, Q., Liu, X., Fu, X., Li, Q., Dou, J., Zhai, G., 2012. Current development in nanoformulations of docetaxel. Expert Opin. Drug Deliv. 9, 975-990.

Tang, X., Wang, G., Shi, R., Jiang, K., Meng, L., Ren, H., Wu, J., Hu, Y., 2016. Enhanced tolerance and antitumor efficacy by docetaxel-loaded albumin nanoparticles. Drug Deliv. 23, 2686-2696.

Tapani, E., Taavitsainen, M., Lindros, K., Vehmas, T., Lehtonen, E., 1996. Toxicity of ethanol in low concentrations. Experimental evaluation in cell culture. Acta Radiol. 37, 923-926.

Tsujino, I., Yamazaki, T., Masutani, M., Sawada, U., Hone, T., 1999. Effect of Tween-80 on cell killing by etoposide in human lung adenocarcinoma cells. Cancer Chemother. Pharmacol. 43, 29-34.

Tuomela, A., Hirvonen, J., Peltonen, L., 2016. Stabilizing agents for drug nanocrystals: effect on bioavailability. Pharmaceutics 8.

van Beilen, J. W., Teixeira de Mottos, M. J., Hellingwerf, K. J., Brul, S., 2014. Distinct effects of sorbic acid and acetic acid on the electrophysiology and metabolism of *Bacillus subtilis*. Appl. Environ. Microbiol. 80, 5918-5926.

van Drooge, D. J., Hinrichs, W. L., Visser, M. R., Frijlink, H. W., 2006. Characterization of the molecular distribution of drugs in glassy solid dispersions at the nano-meter scale, using differential scanning calorimetry and gravimetric water vapour sorption techniques. Int. J. Pharm. 310, 220-229.

Various, Stability Testing of New Drug Substances and Products. FDA, US-Federal Register 68, 65717-65718.

Various, 1997. Desktop X-ray diffractometer "Miniflex". Rigaku J. 14, 29-36.

Vividha Dhapte, P. M., 2015. Advanced in hydrotropic solutions: An updated review. 1, 424-436.

Vo, C. L., Park, C., Lee, B. J., 2013. Current trends and future perspectives of solid dispersions containing poorly water-soluble drugs. Eur. J. Pharm. Biopharm. 85, 799-813.

Wang, J., Yan, Z., Zhuo, K., Lu, J., 1999. Partial molar volumes of some alpha-amino acids in aqueous sodium acetate solutions at 308.15 K. Biophys. Chem. 80, 179-188.

Ward, M. D., Buttry, D. A., 1990. In situ interfacial mass detection with piezoelectric transducers. Science 249, 1000-1007.

Weckman, N. E., McRae, C., Ko Ferrigno, P., Seshia, A. A., 2016. Comparison of the specificity and affinity of surface immobilised Affimer binders using the quartz crystal microbalance. Analyst 141, 6278-6286.

Yhee, J. Y., Jeon, S., Yoon, H. Y., Shim, M. K., Ko, H., Min, J., Na, J. H., Chang, H., Han, H., Kim, J. H., Suh, M., Lee, H., Park, J. H., Kim, K., Kwon, I. C., 2017. Effects of tumor microenvironments on targeted delivery of glycol chitosan nanoparticles. J. Control. Release.

Zhai, G., Wu, J., Xiang, G., Mao, W., Yu, B., Li, H., Piao, L., Lee, L. J., Lee, R. J., 2009. Preparation, characterization and pharmacokinetics of folate receptor-targeted liposomes for docetaxel delivery. J. Nanosci. Nanotechnol. 9, 2155-2161.

Zhang, P., Zhang, H., He, W., Zhao, D., Song, A., Luan, Y., 2016. Disulfide-Linked amphiphilic polymer-docetaxel conjugates assembled redox-sensitive micelles for efficient antitumor drug delivery. Biomacromolecules 17, 1621-1632.

Zheng, J. Y., Keeney, M. P., 2006. Taste masking analysis in pharmaceutical formulation development using an electronic tongue. Int. J. Pharm. 310, 118-124.

What is claimed is:

1. A process for improving the aqueous availability of a material with low water solubility by forming a crystalline solid dispersion (CSD) of the material, wherein the improved aqueous availability is improved aqueous solubility or improved aqueous dispersion, the process comprising the steps:
    (a) forming a solution consisting of the material; one or more acetate salts selected from the group consisting of LiOAc, NaOAc, KOAc, and CsOAc; and glacial acetic acid; and
    (b) removing the acetic acid from the solution from step (a) by freeze-drying to yield the crystalline solid dispersion (CSD) of the compound.

2. The process of claim 1 wherein the improved aqueous availability is improved aqueous dispersion of the material.

3. The process of claim 1 wherein the improved aqueous availability is improved aqueous solubility of the material.

4. The process of claim 1 wherein the material is a bioactive compound.

5. The process of claim 4 the bioactive compound is a pharmaceutical agent.

6. The process of claim 5 wherein the pharmaceutical agent is selected from the group consisting of antibacterials, antifungals, antivirals, and cancer drugs.

7. The process of claim 5 wherein the pharmaceutical agent is a cancer drug.

8. The process of claim 7 wherein the pharmaceutical agent is docetaxel.

9. The process of claim 4 wherein the bioactive compound is an agricultural pesticide selected from the group consisting of insecticides, herbicides, fungicides, and nematicides.

10. The process of claim 1 wherein the material is a compound having a water solubility of about 1 µg/mL to about 500 µg/mL, of about 400 µg/mL to about 300 µg/mL, of about 300 µg/mL to about 200 µg/mL, of about 200 µg/mL to about 100 µg/mL, of about 100 µg/mL to about 50

μg/mL, of about 50 μg/mL to about 25 μg/mL, of about 25 μg/mL to about 10 μg/mL, or of about 10 μg/mL to about 1 μg/mL.

11. The process of claim 1 wherein the material is a compound having a log P value of about 1 to about 2, from about 2 to about 3, from about 3 to about 4, from about 4 to about 5, or from about 5 to about 8.

12. The process of claim 1 wherein the amount of the material in the solution of (a) is about 1 part of the material to about 263 parts (w/w) of glacial acetic acid.

13. The process of claim 1 wherein the amount of the acetate salt in the solution of (a) is about 1 part of the acetate salt to about 18.5 parts of glacial acetic acid (w/w).

14. The process of claim 1 wherein the acetate salt is sodium acetate (NaOAc).

* * * * *